United States Patent
Matlock et al.

(10) Patent No.: US 11,883,618 B2
(45) Date of Patent: Jan. 30, 2024

(54) DILATION CATHETER TIP REMOVAL INSTRUMENT

(71) Applicant: Acclarent, Inc., Irvine, CA (US)

(72) Inventors: George L. Matlock, Pleasanton, CA (US); John H. Thinnes, Jr., Mission Viejo, CA (US); Jordan R. Trott, Redondo Beach, CA (US); Karthick Ramyan Mohan, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 680 days.

(21) Appl. No.: 16/553,384

(22) Filed: Aug. 28, 2019

(65) Prior Publication Data
US 2020/0108238 A1 Apr. 9, 2020

Related U.S. Application Data
(60) Provisional application No. 62/741,605, filed on Oct. 5, 2018.

(51) Int. Cl.
*A61M 29/02* (2006.01)
*B26D 1/08* (2006.01)
(Continued)

(52) U.S. Cl.
CPC .............. *A61M 29/02* (2013.01); *B26D 1/08* (2013.01); *A61M 3/0295* (2013.01);
(Continued)

(58) Field of Classification Search
CPC . B26D 1/08; B26D 3/192; B26D 3/16; B26D 3/169; B26D 3/166; A61B 29/02
See application file for complete search history.

(56) References Cited

U.S. PATENT DOCUMENTS
5,791,051 A * 8/1998 Schmidt ................. A24F 13/26
30/113
5,992,022 A * 11/1999 Carrera Moya ........ A24F 13/24
30/113
(Continued)

FOREIGN PATENT DOCUMENTS
GB      2365811 A * 2/2002 ............. B23D 21/10
JP   H0670983 A * 3/1994
(Continued)

OTHER PUBLICATIONS
International Search Report and Written Opinion dated Nov. 13, 2019 for International Application No. PCT/IB2019/058303, 19 pages.

(Continued)

*Primary Examiner* — Jennifer S Matthews
(74) *Attorney, Agent, or Firm* — Frost Brown Todd LLP

(57) ABSTRACT

A method of using an apparatus including a base housing, an actuator, and a blade. The base housing defines an upwardly presented support surface. The base housing also defines a distally oriented tip receiving recess. The distally oriented tip receiving recess is sized and configured to receive a bulbous distal tip of a dilation catheter. The actuator is movably coupled with the base housing. The blade us secured to the actuator. The actuator is operable to move the blade downwardly relative to the base housing. The blade is configured to sever a portion of a dilation catheter along a plane longitudinally interposed between the support surface and the tip receiving recess to thereby sever the bulbous distal tip of the dilation catheter in response to movement of the actuator relative to the base housing.

19 Claims, 19 Drawing Sheets

(51) Int. Cl.
 *A61M 3/02* (2006.01)
 *A61M 25/09* (2006.01)
(52) U.S. Cl.
 CPC . *A61M 25/09041* (2013.01); *A61M 2205/583* (2013.01); *A61M 2205/587* (2013.01); *A61M 2210/0675* (2013.01); *A61M 2210/0681* (2013.01)

(56) References Cited

U.S. PATENT DOCUMENTS

| | | | |
|---|---|---|---|
| 9,155,492 | B2 | 10/2015 | Jenkins et al. |
| 2001/0032390 | A1 | 10/2001 | Davison |
| 2007/0175048 | A1* | 8/2007 | Holley .................. B26D 3/169 30/278 |
| 2008/0183128 | A1 | 7/2008 | Morriss et al. |
| 2008/0236358 | A1* | 10/2008 | Vitullo .................. A61M 25/01 83/663 |
| 2010/0274188 | A1 | 10/2010 | Chang et al. |
| 2011/0004057 | A1 | 1/2011 | Goldfarb et al. |
| 2013/0274715 | A1* | 10/2013 | Chan .................. A61M 29/00 604/514 |
| 2014/0074141 | A1 | 3/2014 | Johnson et al. |
| 2014/0364725 | A1 | 12/2014 | Makower |
| 2016/0008083 | A1 | 1/2016 | Kesten et al. |
| 2016/0287059 | A1* | 10/2016 | Ha .................... A61M 25/0041 |
| 2017/0056632 | A1 | 3/2017 | Jenkins et al. |
| 2017/0120020 | A1 | 5/2017 | Lin et al. |
| 2018/0214216 | A1 | 8/2018 | Sema et al. |
| 2019/0015645 | A1 | 1/2019 | Matlock et al. |
| 2019/0192176 | A1 | 6/2019 | Palushi et al. |
| 2019/0192177 | A1 | 6/2019 | Palushi et al. |
| 2021/0315599 | A1* | 10/2021 | Vale .................. A61B 5/02007 |

FOREIGN PATENT DOCUMENTS

| | | |
|---|---|---|
| JP | H06-84402 U | 12/1994 |
| JP | H10-151598 A | 6/1998 |
| JP | 2018-511408 A | 4/2018 |

OTHER PUBLICATIONS

Japanese Notification of Reasons for Refusal dated May 24, 2023, for Application No. 2021-518465, 7 pages.
Extended European Search Report dated Sep. 7, 2023, for Application No. 23174490.5, 9 pages.

* cited by examiner

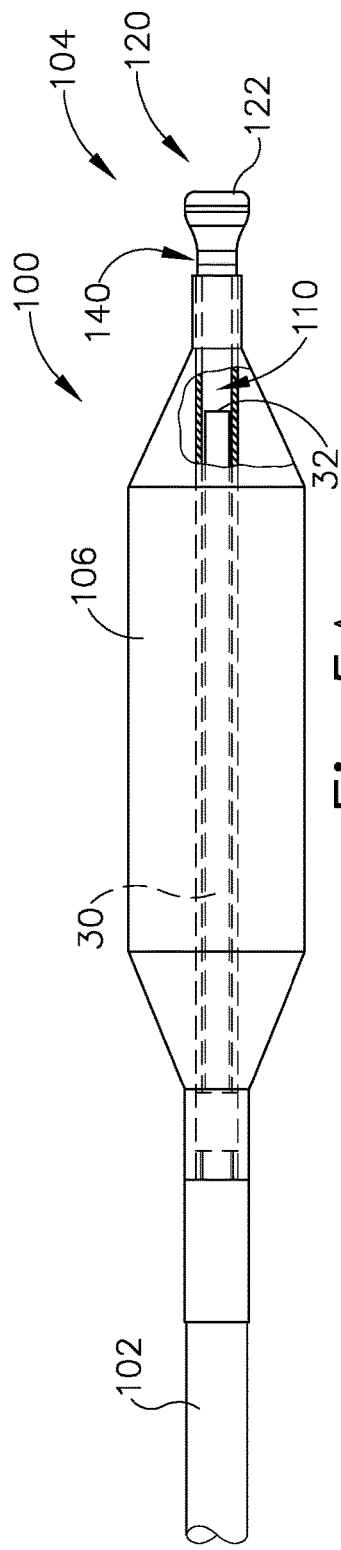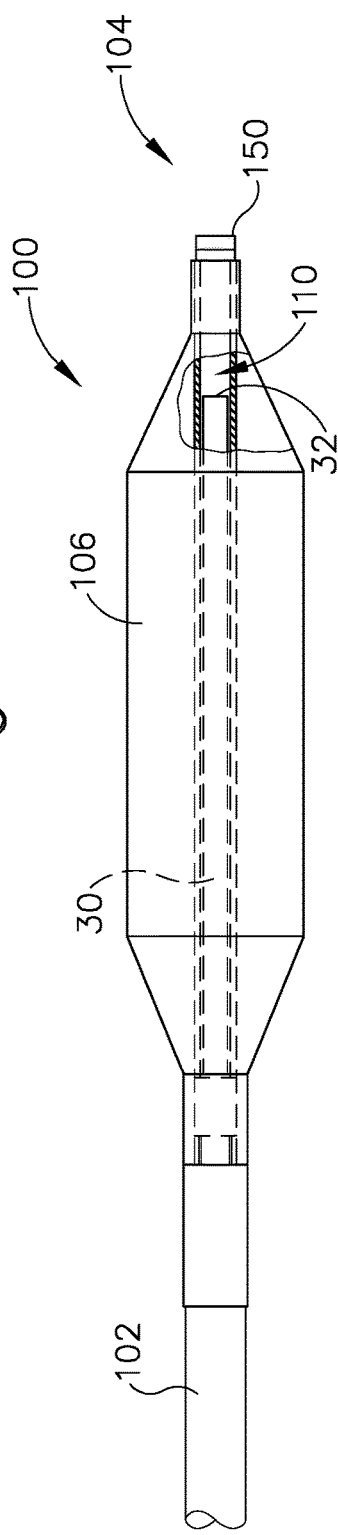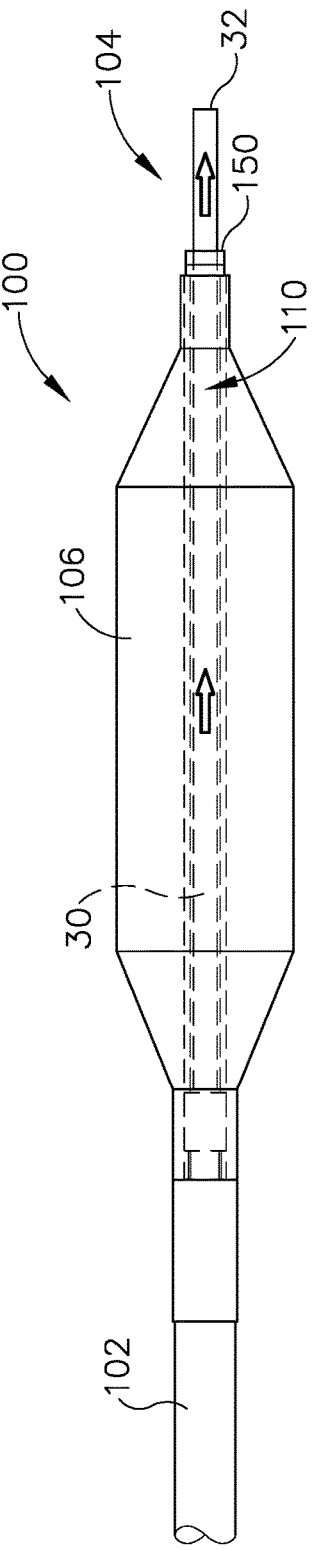

DILATION CATHETER TIP REMOVAL INSTRUMENT

PRIORITY

This application claims priority to U.S. Provisional Pat. App. No. 62/741,605, entitled "Dilation Catheter Tip Removal Instrument," filed Oct. 5, 2018, the disclosure of which is incorporated by reference herein in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, California.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, California.

Some dilation catheters may be particularly configured to transition between two modes particularly suited for two different kinds of medical procedures—one mode particularly suited for Eustachian tube dilation procedures and another mode particularly suited for sinus ostium dilation procedures. An example of such a dilation catheter is described in U.S. Pub. No. 2017/0056632, entitled "Dilation Catheter with Expandable Stop Element," published Mar. 2, 2017, issued as U.S. Pat. No. 10,512,763 on Dec. 24, 2019, the disclosure of which is incorporated by reference herein.

While several systems and methods have been made and used in ENT procedures, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5A depicts a side elevational view of the distal portion of the dilation catheter of FIG. 4, with the bulb tip secured at the distal end of the dilation catheter, and with a guidewire at a proximal position within the dilation catheter;

FIG. 5B depicts a side elevational view of the distal portion of the dilation catheter of FIG. 4, with the bulb tip removed from the distal end of the dilation catheter, and with the guidewire at a proximal position within the dilation catheter;

FIG. 5C depicts a side elevational view of the distal portion of the dilation catheter of FIG. 4, with the bulb tip removed from the distal end of the dilation catheter, and with the guidewire at a distal position such that a distal end of the guidewire is distal to the distal end of the dilation catheter;

Figure 1A:
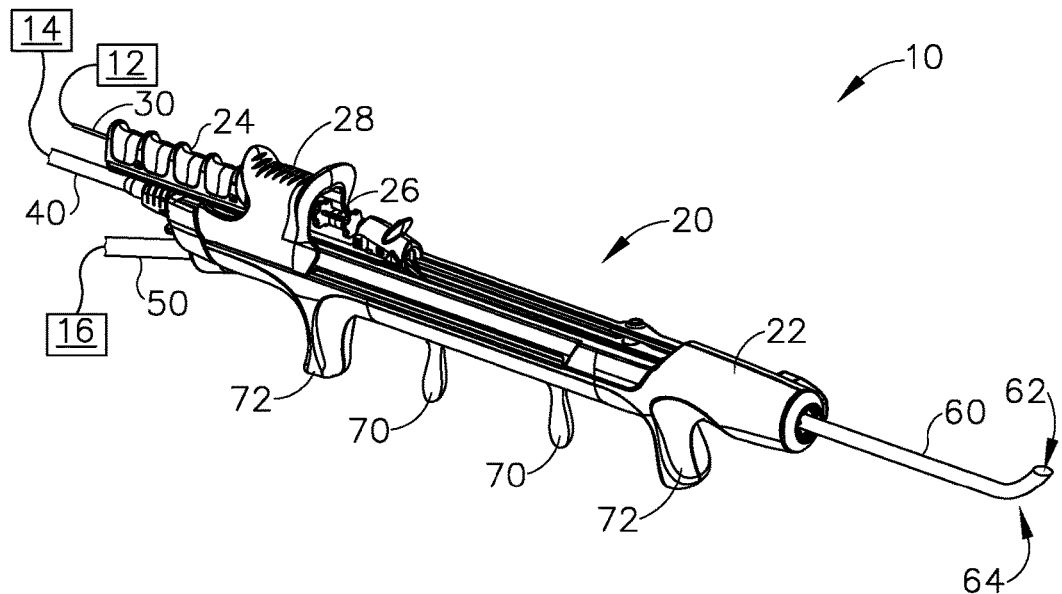
FIG. 1A depicts a perspective view of an exemplary dilation instrument system including a dilation instrument having a guidewire and a dilation catheter, showing the guidewire in a proximal position, and the dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. EXEMPLARY DILATION INSTRUMENT SYSTEM

FIGS. 1A-1D show an exemplary dilation instrument system (10) that may be used to dilate the ostium of a paranasal sinus in a human patient; to dilate some other passageway associated with drainage of a paranasal sinus in a human patient; to dilate a Eustachian tube in a human patient; or to dilate some other anatomical passageway (e.g., within the ear, nose, or throat, etc.) in a human patient. Dilation instrument system (10) of this example comprises a guidewire power source (12), an inflation fluid source (14), an irrigation fluid source (16), and a dilation instrument (20). In some versions, guidewire power source (12) comprises a source of light. In some other versions, guidewire power source (12) is part of an image guided surgery (IGS) system. Inflation fluid source (14) may comprise a source of saline or any other suitable source of fluid. Irrigation fluid source (16) may also comprise a source of saline or any other suitable source of fluid.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22).

A guide catheter (60) extends distally from handle body (22). Guide catheter (60) includes an open distal end (62) and a bend (64) formed proximal to open distal end (62). In some versions, dilation instrument (20) is configured to removably receive several different kinds of guide catheters (60), each guide catheter (60) having a different angle formed by bend (64). Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

By way of further example only, guide catheter (60) may be configured and operable in accordance with at least some of the teachings of U.S. patent application Ser. No. 15/852,470, entitled "Dilation Instrument with Guide Catheter Type Sensor," filed Dec. 22, 2017, now abandoned, the disclosure of which is incorporated by reference herein; U.S. Pub. No. 2017/0120020, entitled "Apparatus for Bending Malleable Guide of Surgical Instrument," published May 4, 2017, issued as U.S. Pat. No. 10,137,286 on Nov. 27, 2019, the disclosure of which is incorporated by reference herein; and/or U.S. patent application Ser. No. 16/032,471, entitled "Adjustable Instrument for Dilation of Anatomical Passageway," filed Jul. 11, 2018, issued as U.S. Pat. No. 10,874,839 on Dec. 29, 2020, the disclosure of which is incorporated by reference herein.

Figure 1B:
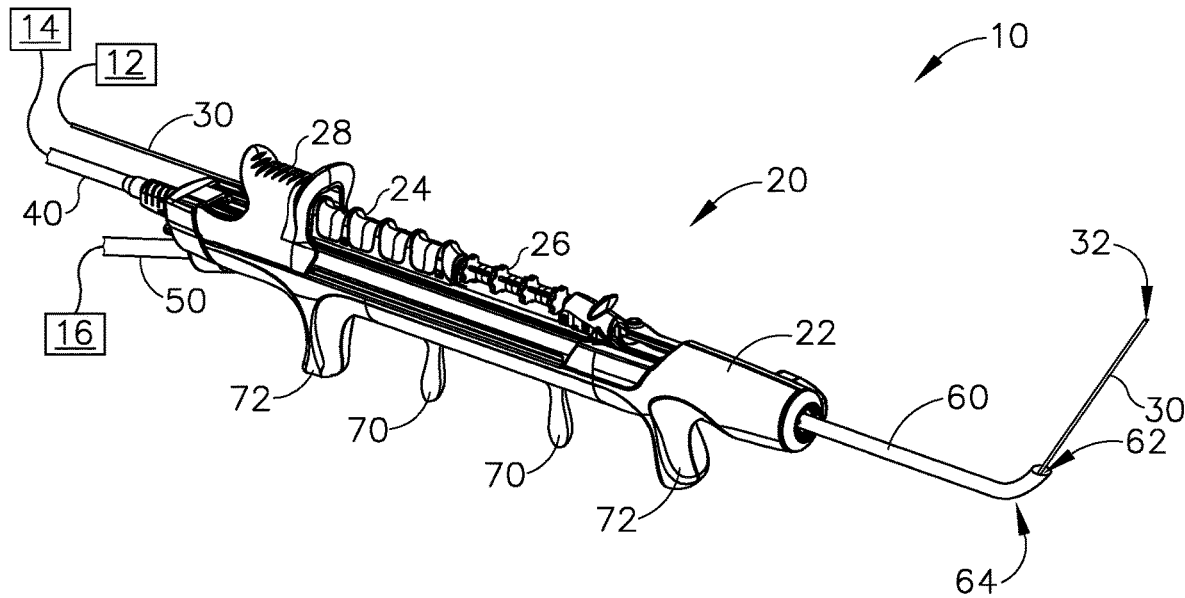
FIG. 1B depicts a perspective view of the dilation instrument system of FIG. 1A, showing the guidewire in a distal position, and the dilation catheter in the proximal position.

A guidewire (30) is coaxially disposed in guide catheter (60). Guidewire slider (24) is secured to guidewire (30). Translation of guidewire slider (24) relative to handle body (22) from a proximal position (FIG. 1A) to a distal position (FIG. 1B) thus causes corresponding translation of guidewire (30) relative to handle body (22) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

By way of further example only, guidewire (30) may be configured and operable in accordance with at least some of the teachings of U.S. Pub. No. 2018/0214216, entitled "Navigation Guidewire with Interlocked Coils," published Aug. 2, 2018, issued as U.S. Pat. No. 10,610,308 on Apr. 7, 2020, the disclosure of which is incorporated by reference herein; U.S. Pat. No. 9,155,492, entitled "Sinus Illumination Lightwire Device," issued Oct. 13, 2015, now abandoned, the disclosure of which is incorporated by reference herein; U.S. patent application Ser. No. 15/852,530, entitled "Reusable Navigation Guidewire," filed Dec. 22, 2017, the disclosure of which is incorporated by reference herein; U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein; and/or U.S. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

Figure 1C:
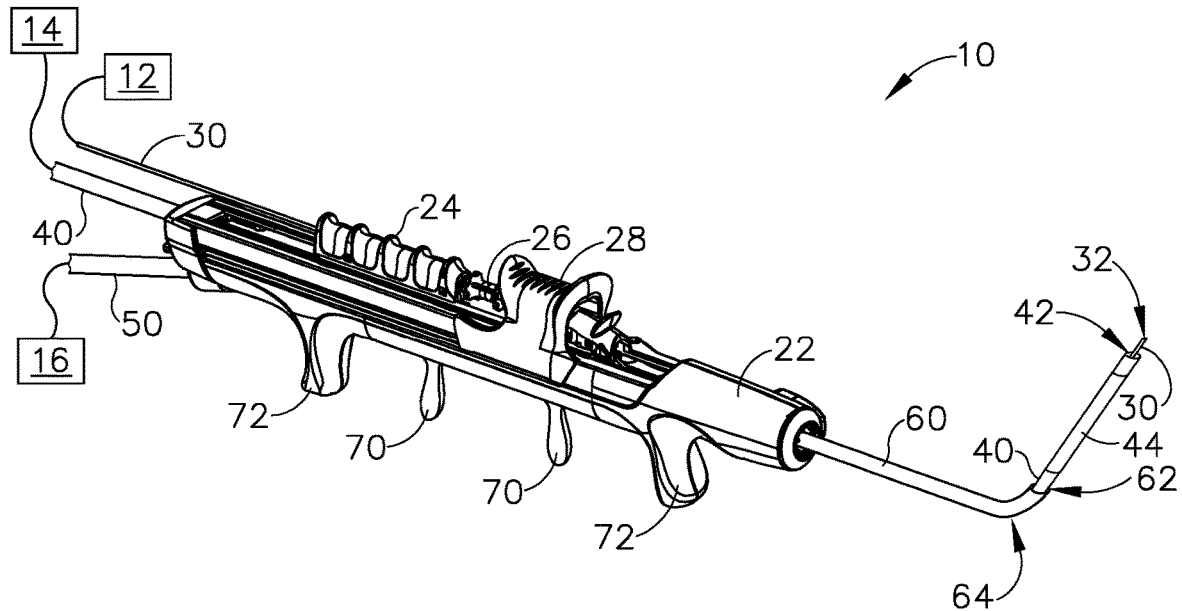
FIG. 1C depicts a perspective view of the dilation instrument system of FIG. 1A, showing the guidewire in the distal position, the dilation catheter in a distal position, and a dilator in a non-dilated state.
Figure 1D:
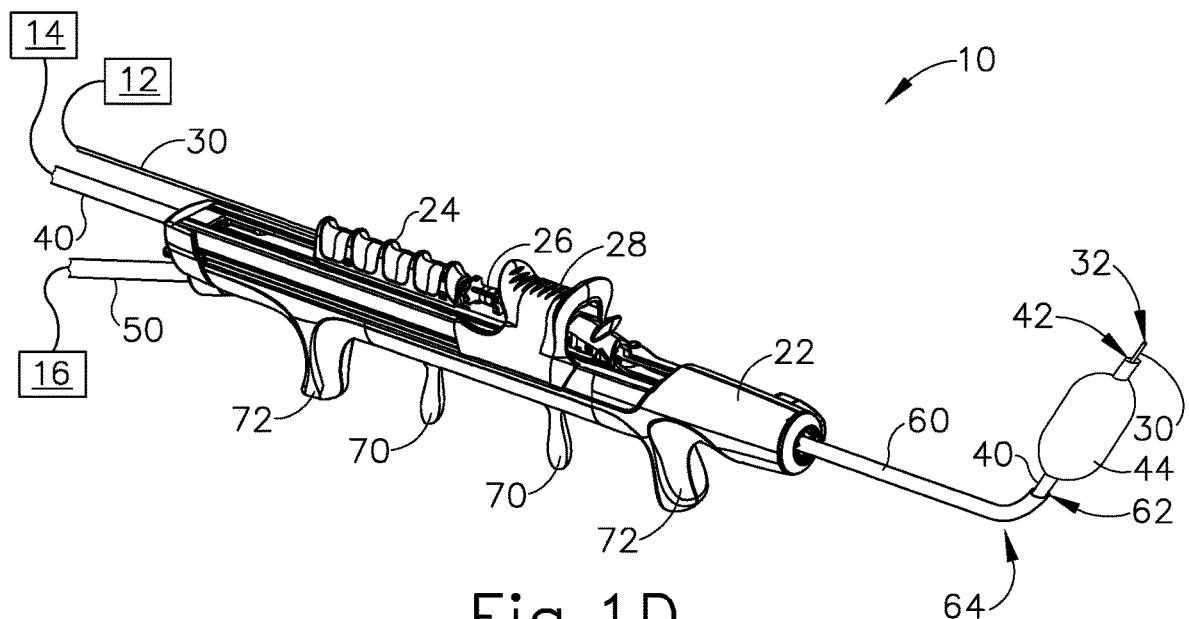
FIG. 1D depicts a perspective view of the dilation instrument system of FIG. 1A, showing the guidewire in the distal position, the dilation catheter in the distal position, and the dilator in a dilated state.

A dilation catheter (40) is coaxially disposed in guide catheter (60). Dilation catheter slider (28) is secured to dilation catheter (40). Translation of dilation catheter slider (28) relative to handle body (22) from a proximal position (FIG. 1B) to a distal position (FIG. 1C) thus causes corresponding translation of dilation catheter (40) relative to handle body (22) from a proximal position (FIG. 1B) to a distal position (FIG. 1C). When dilation catheter (40) is in a distal position, a distal portion of dilation catheter (40) protrudes distally from open distal end (62) of guide catheter (60). Dilation catheter (40) of the present example comprises a non-extensible balloon (44) located just proximal to open distal end (42) of dilation catheter (40). Balloon (44) is in fluid communication with inflation fluid source (14). Inflation fluid source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In the non-inflated state, balloon (44) is configured to be inserted into a constricted anatomical passageway (e.g., paranasal sinus ostium, Eustachian tube, etc.). In the inflated state, balloon (44) is configured to dilate the anatomical passageway in which balloon (44) is inserted. Other features and operabilities that may be incorporated into dilation catheter (40) will be described in greater detail below.

In some versions, inflation fluid source (14) comprises a manually actuated source of pressurized fluid. In some such versions, the manually actuated source of pressurized fluid may be configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after a dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via irrigation tube (50), to enable irrigation of the anatomical site in the patient. By way of example only, a dedicated irrigation catheter may be configured and operable in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein.

II. EXEMPLARY DILATION PROCEDURES

As noted above, dilation instrument system (10) may be used to dilate a drainage passageway associated with a paranasal sinus, a Eustachian tube, and/or any other passageway in the ear, nose, or throat of a patient. The following describes two merely illustrative examples of dilation procedures in which dilation instrument system (10) may be used. The following examples are not intended to be limiting. Other procedures in which dilation instrument system (10) may be used will be apparent to those of ordinary skill in the art in view of the teachings herein.

A. Exemplary Sinus Ostium Dilation Procedure

Figure 2A:
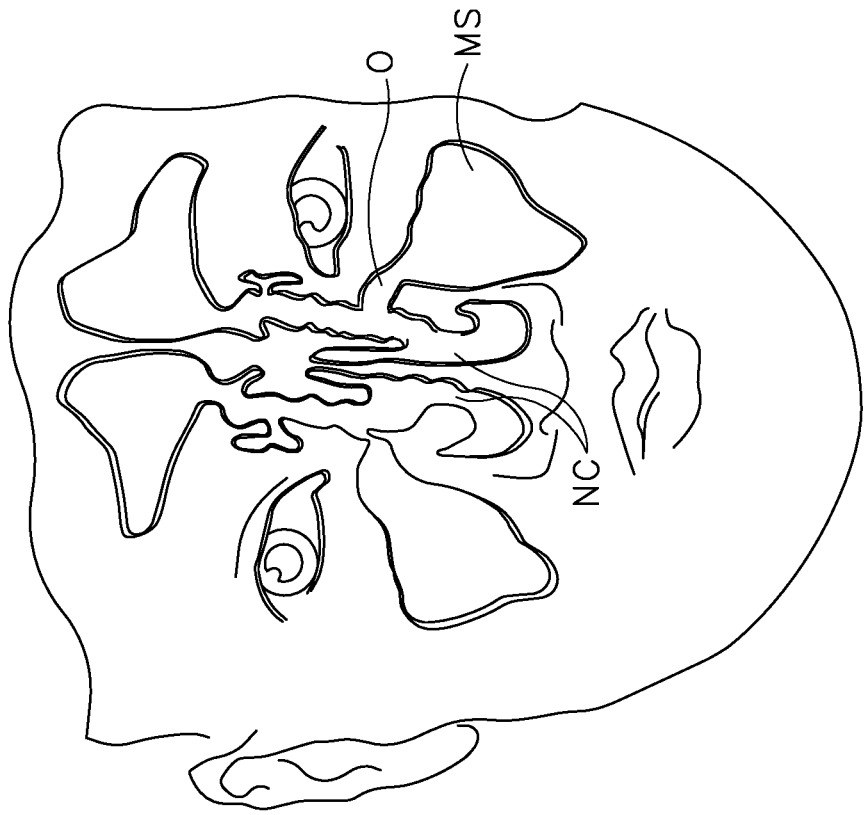
FIG. 2A depicts a schematic view of a guide catheter, guidewire, and dilation catheter of the dilation instrument system of FIG. 1A inserted through the nose of a patient, with the guidewire positioned in a paranasal sinus cavity, and the dilator being expanded to dilate an ostium of the paranasal sinus cavity.
Figure 2B:
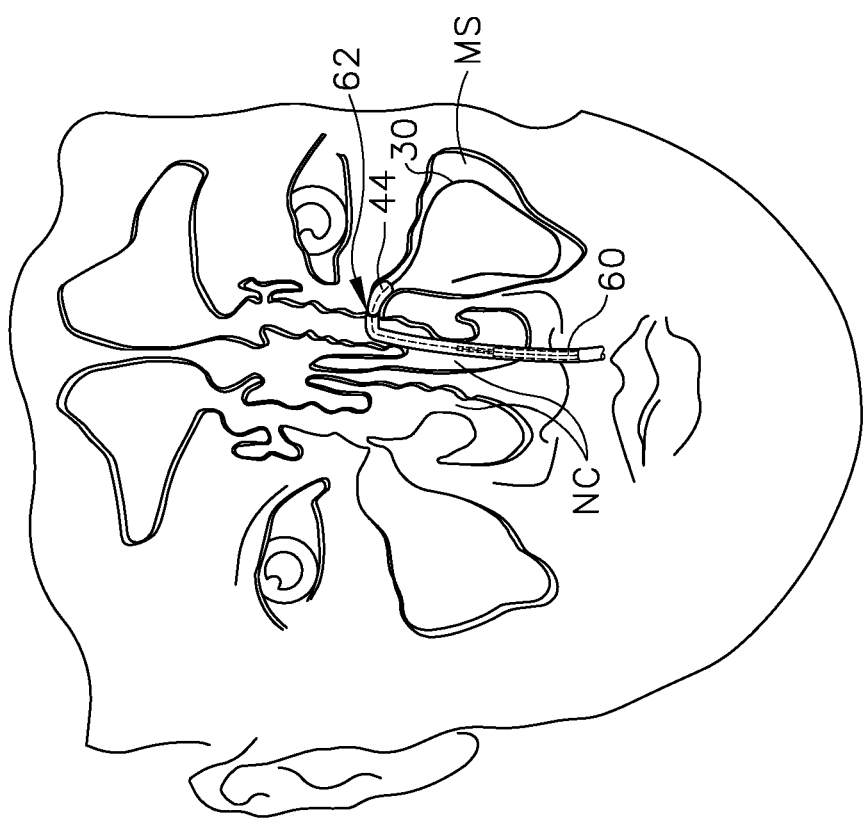
FIG. 2B depicts a schematic view of the patient of FIG. 2A, with the ostium of the paranasal sinus cavity in a dilated state.

FIGS. 2A-2B show portions of dilation instrument system (10) being used in an exemplary procedure do dilate an ostium (O) of a maxillary sinus (MS) of a patient. As shown in FIG. 2A, guide catheter (60) is positioned in the nasal cavity (NC) of the patient and is oriented to direct dilation catheter (40) into the ostium (O) of the maxillary sinus (MS). Guidewire (30) is advanced into the maxillary sinus (MS) at the stage depicted in FIG. 2A, and balloon (44) is inflated at the stage depicted in FIG. 2A.

In the steps leading up to the stage depicted in FIG. 2A, dilation catheter (40) may be fully retracted into guide catheter (60), and guidewire (30) may be retracted into dilation catheter (40), as guide catheter (60) is initially inserted into the nasal cavity (NC). Guide catheter (60) may then be manipulated to orient distal end (62) toward the ostium (O) of the maxillary sinus (MS). This may be performed under visualization from an endoscope or otherwise. Guidewire (30) may then be advanced through the ostium (O) and into the maxillary sinus (MS). In versions where guidewire (30) has an illuminating distal end, the position of guidewire (30) in the maxillary sinus (MS) may be verified by observing transillumination effects through the cheek of the patient over the maxillary sinus (MS). In versions where guidewire (30) includes a navigation sensor, an image guided surgery navigation system (or other kind of navigation system) may be used to verify that guidewire (30) is in the maxillary sinus (MS). Once guidewire (30) has been positioned, dilation catheter (40) may be advanced distally along guidewire (30), with further guidance from guide catheter (60), until balloon (44) is positioned in the ostium (O) of the maxillary sinus (MS). The balloon (44) is then inflated to thereby dilate the ostium (O) of the maxillary sinus (MS).

After balloon (44) has been inflated and deflated a sufficient number of times within the ostium (O), dilation instrument system (10) is removed from the patient. The patient then has a dilated ostium (O) as shown in FIG. 2B. The dilated ostium (O) may provide improved ventilation to the maxillary sinus (MS) from the nasal cavity (NC) and/or improved drainage from the maxillary sinus (MS) into the nasal cavity (NC).

B. Exemplary Eustachian Tube Dilation Procedure

Figure 3A:
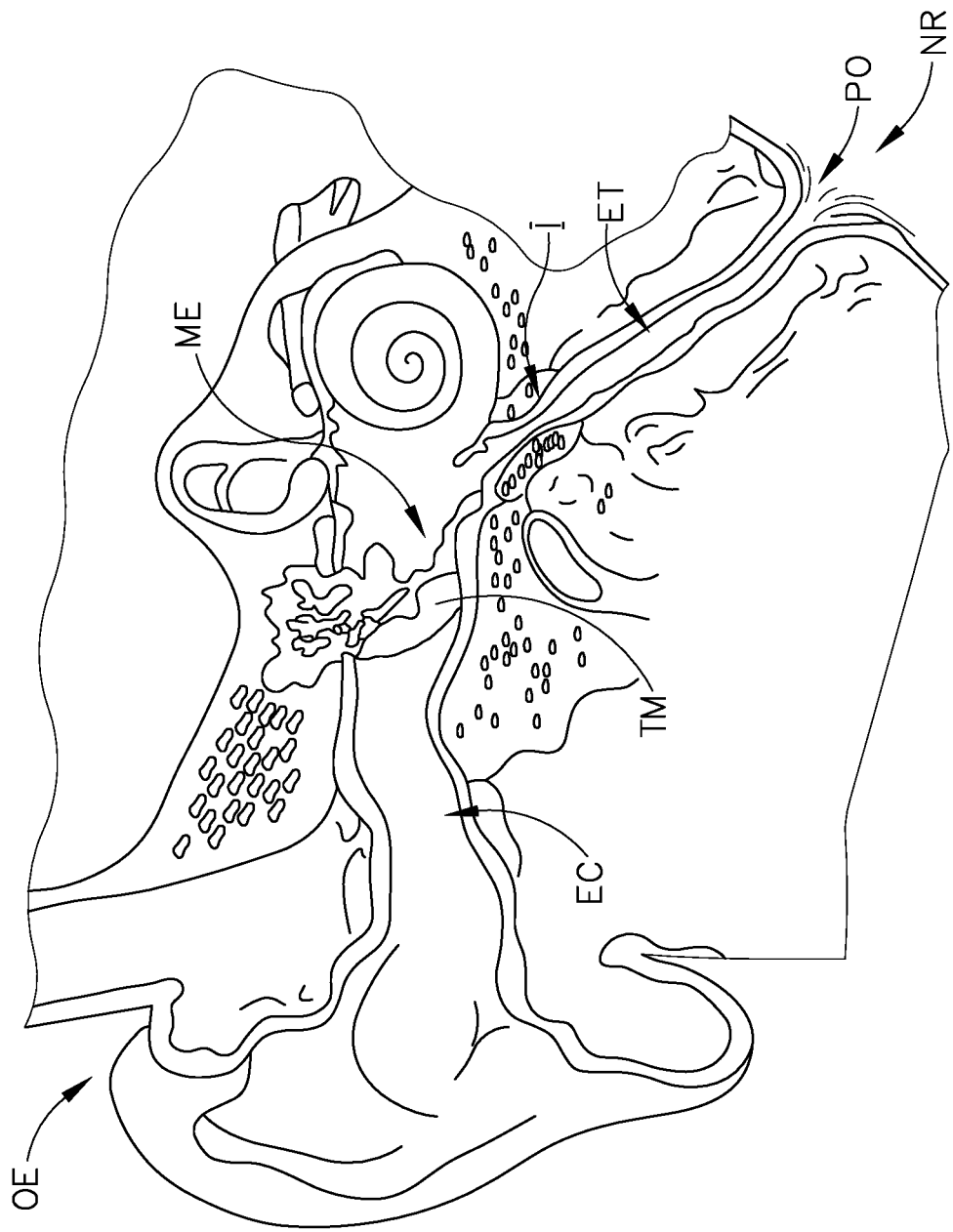
FIG. 3A depicts a cross-sectional view of a human ear showing the inner, middle and outer ear portions and the Eustachian tube connecting the middle ear with the nasopharynx region of the throat.

FIG. 3A shows anatomical structures associated with a patient's ear, including the outer ear (OE), the ear canal (EC), the tympanic membrane (TM), the middle ear (ME), and the Eustachian tube (ET). The Eustachian tube (ET) is in fluid communication with the nasopharynx via the pharyngeal ostium (PO). The isthmus (I) is a narrowed region (e.g., approximately 1 mm in diameter) between the Eustachian tube (ET) and the middle ear (ME). The Eustachian tube (ET) provides a pathway for ventilation from the nasopharynx to the middle ear (ME); and for drainage from the middle ear (ME) to the nasopharynx. When functioning properly, the Eustachian tube (ET) may open for a fraction of a second periodically in response to swallowing or yawning. In so doing, it allows air into the middle ear (ME) to replace air that has been absorbed by the middle ear lining (mucous membrane) or to equalize pressure changes occurring on altitude changes. In instances where fluid is built up in the middle ear (ME), an opened Eustachian tube (ET) also provides a pathway for such fluid to drain from the middle ear (ME) into the nasopharynx.

Figure 3B:
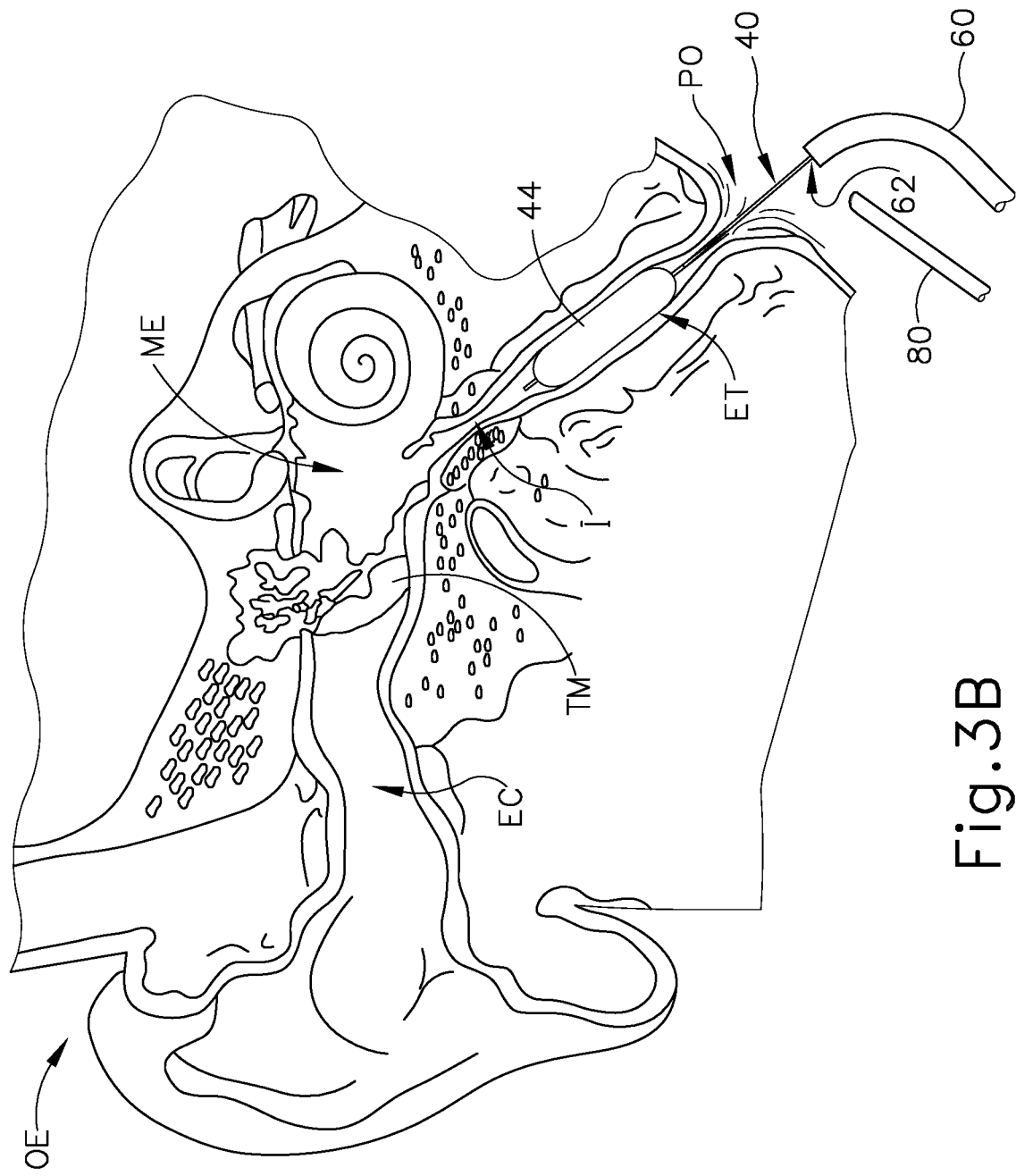
FIG. 3B depicts a cross-sectional view of the human ear of FIG. 3A, with the dilation catheter of the dilation instrument system of FIG. 1A inserted in the Eustachian tube, and the dilator being expanded to dilate the Eustachian tube.

In scenarios where the Eustachian tube (ET) remains persistently blocked or fails to open when it should, it may be desirable to dilate the Eustachian tube (ET). As shown in FIG. 3B, this may be carried out using dilation instrument system (10) by inserting guide catheter (60) through a patient's nose or mouth and positioning guide catheter (60) in the nasopharynx such that distal end (62) is oriented toward the pharyngeal ostium (PO). This may be performed under visualization from an endoscope (80), if desired. Dilation catheter (40) may be advanced through guide catheter (60) to position balloon (44) within the Eustachian tube (ET), and the balloon (44) may then be inflated to thereby dilate the Eustachian tube (ET).

When dilation catheter (40) is advanced through guide catheter (60) to position balloon (44) within the Eustachian tube (ET), it may be necessary to take great care to avoid traversing the isthmus (I). This may ensure that instrumentation does not enter the middle ear (ME) and thereby damage the sensitive anatomical structures within the middle ear (ME). To that end, in the present example, guidewire (30) is not advanced through Eustachian tube (ET) before dilation catheter (40) is advanced into the Eustachian tube (ET). This is because guidewire (30) has a relatively small outer diameter, which may present a substantial risk of guidewire (30) being accidentally advanced through the isthmus (I) and into the middle ear (ME). It may also be desirable to include a structural feature at the distal end of dilation catheter (40) to prevent the distal end of dilation catheter (40) from traversing the isthmus (I). An example of such a structural feature is described in greater detail below.

III. EXEMPLARY ALTERNATIVE DILATION CATHETER

It may be desirable to provide a dilation instrument system (10) with a single dilation catheter that may be used to dilate sinus ostia (O) and other passageways associated with drainage of paranasal sinus cavities and also a Eustachian tube. As noted above, it may be desirable to include a structural feature at the distal end of dilation catheter (40) to prevent the distal end of dilation catheter (40) from traversing the isthmus (I), thereby preventing the distal end of dilation catheter (40) from inadvertently damaging delicate anatomical structures in the middle ear (ME). However, including such a structure on the distal end of dilation catheter (40) prevent the distal end of dilation catheter from traversing a sinus ostium (O) or other passageway associated with drainage of a paranasal sinus. In other words, in order to be large enough to effectively prevent traversal of the isthmus (I), the distal end structure of dilation catheter (40) may be too large to pass through a sinus ostium (O) or other passageway associated with drainage of a paranasal sinus.

In view of the foregoing, it may be desirable to provide a version of dilation catheter (40) that is capable of operating in two different structural modes—one with an enlarged distal end structure and one with a non-enlarged distal end structure. This may facilitate use of the same single dilation catheter in sinus ostium (O) dilation procedures and in Eustachian tube (ET) dilation procedures, while preventing inadvertent traversal of the isthmus (I) during Eustachian tube (ET) dilation procedures, and while enabling traversal of a sinus ostium (O) during sinus ostium (O) dilation procedures. Examples such variations of dilation catheter (40) are described in greater detail below.

Figure 4:
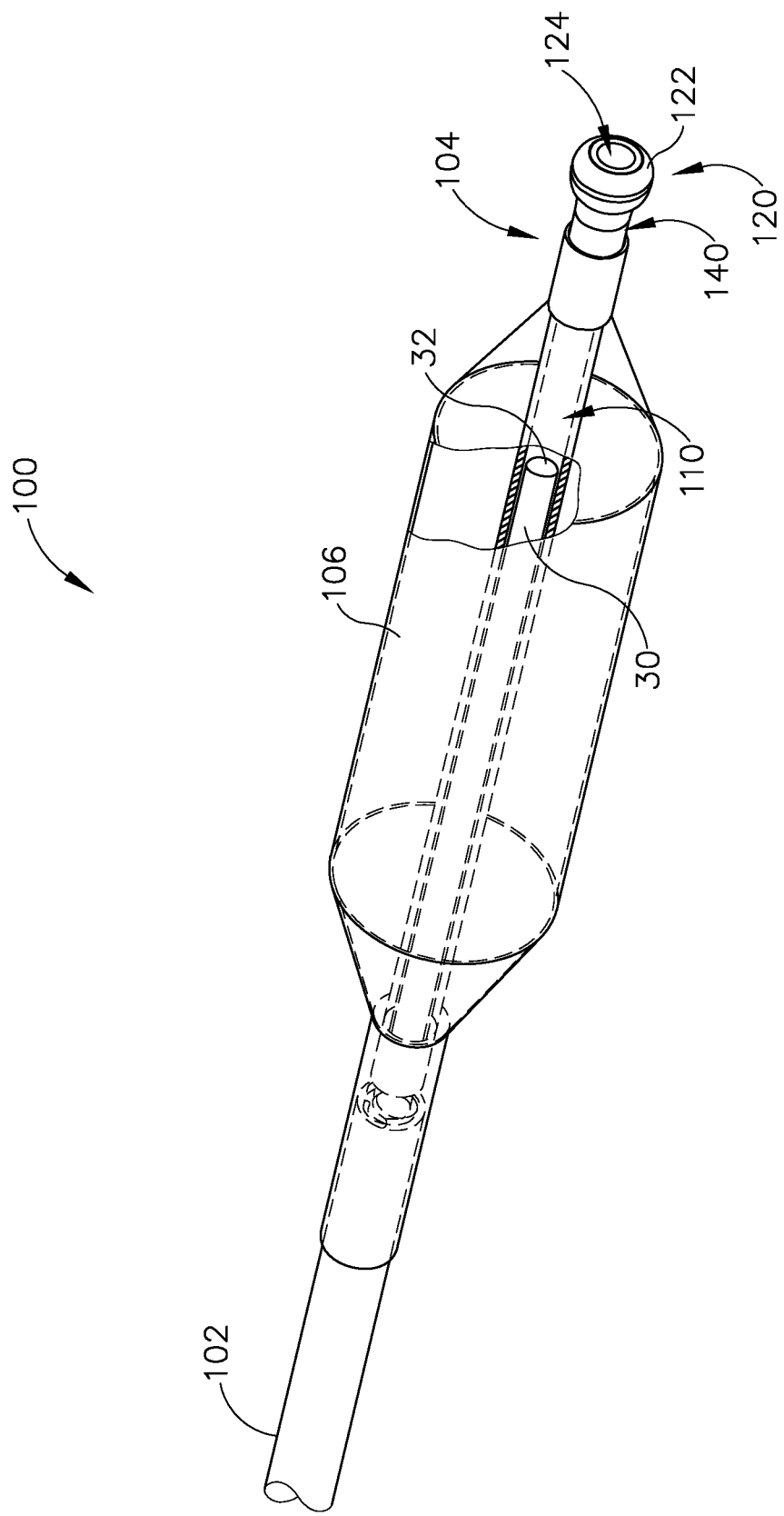
FIG. 4 depicts a perspective view of a distal portion of an exemplary alternative dilation catheter that may be readily incorporated into the dilation instrument system of FIG. 1A, with a bulb tip secured at the distal end of the dilation catheter.
Figure 6:
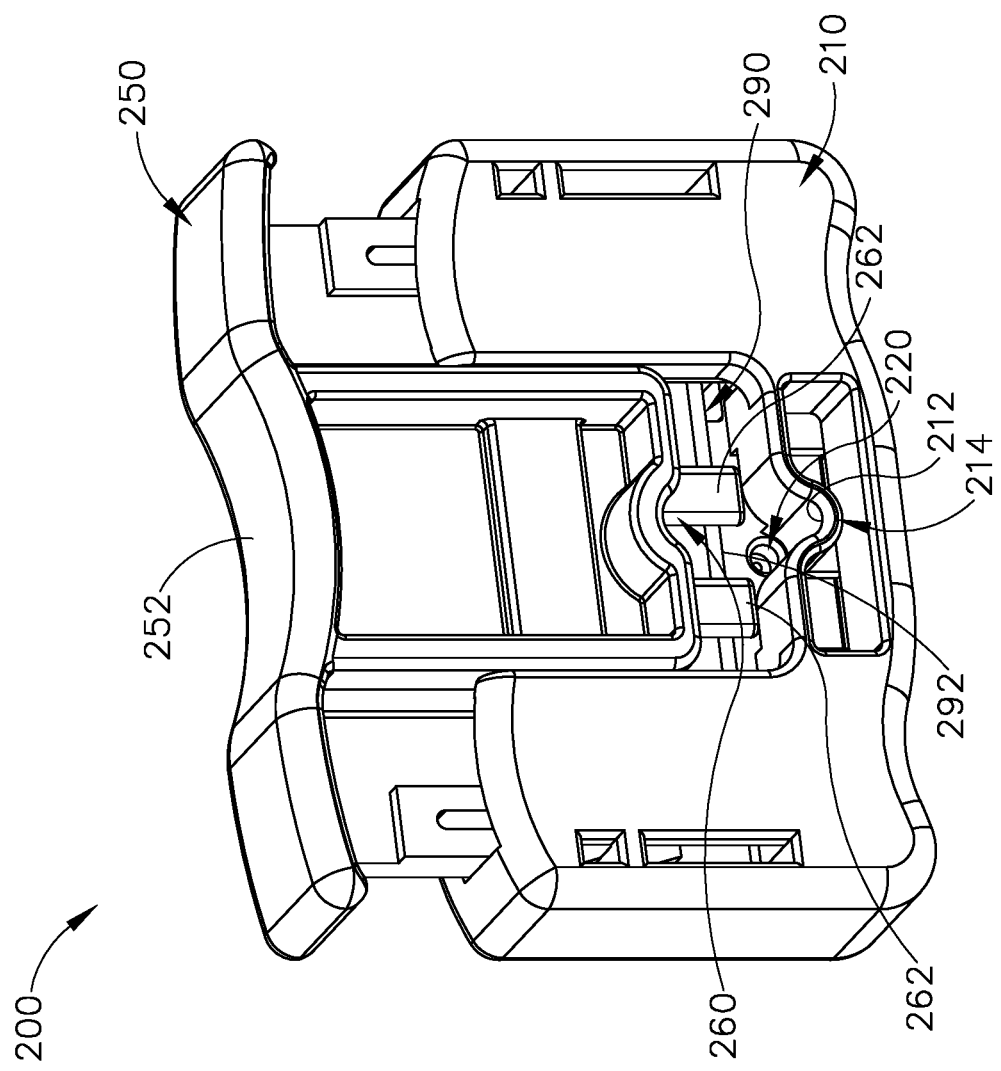
FIG. 6 depicts a perspective view of an exemplary instrument that may be used to remove the bulb tip of the dilation catheter of FIG. 4.
Figure 7:
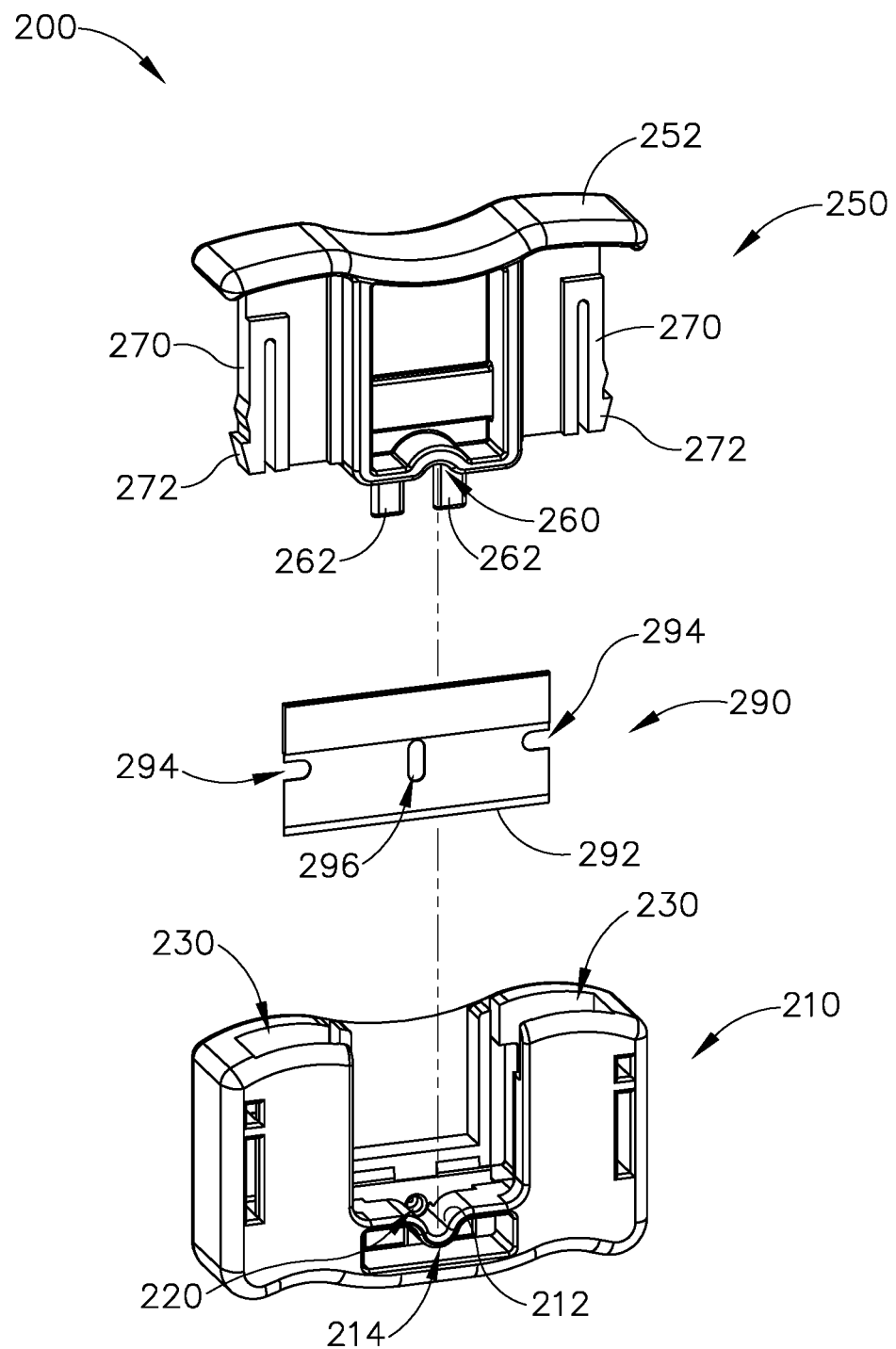
FIG. 7 depicts an exploded perspective view of the instrument of FIG. 6.
Figure 8:
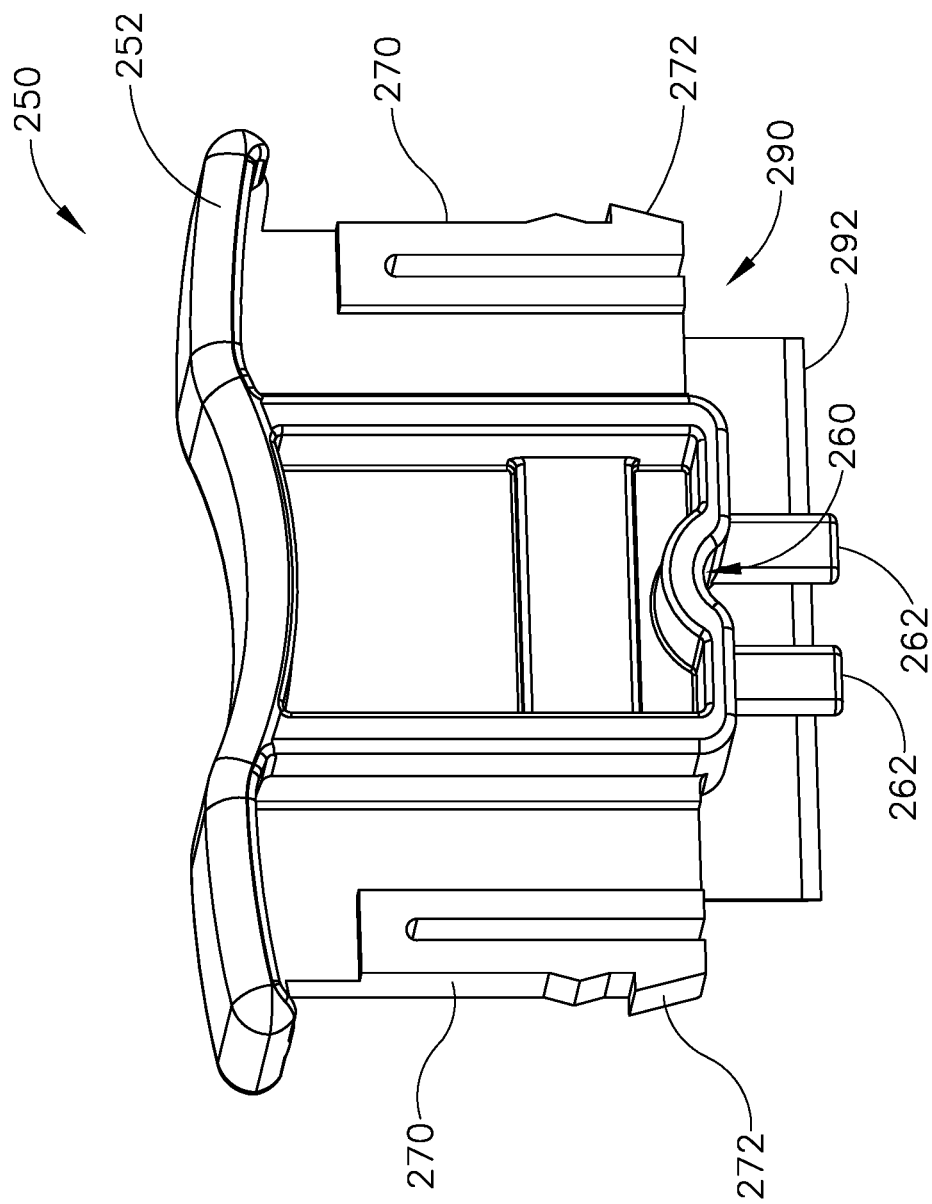
FIG. 8 depicts a perspective view of an actuator and blade assembly of the instrument of FIG. 6.

FIGS. 4-5C depict a distal portion of an exemplary alternative dilation catheter (100). Dilation catheter (100) of this example may be readily incorporated into dilation instrument system (10) in place of dilation catheter (40). Dilation catheter (100) of this example comprises a flexible shaft (102) with a distal end (104). An inflatable balloon (106) is secured to shaft (102) near distal end (104). Flexible shaft (102) defines a guidewire lumen (110) that slidably receives guidewire (30). Flexible shaft (102) also defines an inflation lumen (not shown) that provides a pathway for communication of fluid between inflation fluid source (14) and balloon (106).

As shown in FIG. 4, distal end (104) includes a bulbous tip (120), which is secured to the distal end of flexible shaft (102). Bulbous tip (120) includes a bulbous body (122) defining an opening (124). Bulbous body (122) is sized such that bulbous body (122) is too large to pass through an isthmus (I) between a Eustachian tube (ET) and a middle ear (ME). By way of example only, bulbous body (122) may have an outer diameter that is larger than 1 mm, such as 2 mm, 3 mm, or larger. In any case, bulbous body (122) has an outer diameter that is larger than the outer diameter of the distal portion of flexible shaft (102) to which bulbous body (122) is secured. In some versions, bulbous body (122) is shaped like a blueberry. In some other versions, bulbous body (122) is spherical. Alternatively, bulbous body (122) may have any other suitable shape.

In the present example, bulbous body (122) is solid and is formed of a material (e.g., plastic, etc.) that has sufficient rigidity to prevent bulbous body (122) from compressing when bulbous body (122) is pushed into an isthmus (I) of a Eustachian tube (ET) via the Eustachian tube (ET). Bulbous body (122) is thus strong enough to provide a hard stop when an operator advances dilation catheter (100) into a Eustachian tube (ET) to the point where bulbous body (122) engages the isthmus (I). However, bulbous body (122) may still be soft enough to prevent damage to the isthmus (I) when bulbous body (122) engages the isthmus (I) when dilation catheter is inserted into the Eustachian tube (ET).

Opening (124) is in fluid communication with lumen (110) of shaft (102). Opening (124) and lumen (110) thus provide a ventilation pathway for the region of the Eustachian tube (ET) that is distal to balloon (106) when balloon (106) is inflated to dilate the Eustachian tube (ET). In some versions, the diameter of opening (124) is smaller than the outer diameter of guidewire (30), such that bulbous tip (120) prevents distal end (32) of guidewire (30) from exiting distal end (104) of dilation catheter (100) when bulbous tip (120) is secured at distal end (104) of dilation catheter (100). By way of example only, in some versions opening (124) has a diameter of approximately 0.8 mm, with guidewire (30) having an outer diameter of approximately 0.94 mm, and with lumen (110) having a diameter of at least approximately 1 mm.

Dilation catheter (100) also includes a mark (140) that provides a visual indication between the distal end of balloon (106) and the proximal end of bulbous tip (120). In some versions, mark (140) simply provides visual guidance to an operator where to cut dilation catheter (100) when the operator wishes to remove bulbous tip (120) as described in greater detail below. In some other versions, dilation catheter (100) may also include perforations or other weakening structural features that facilitate frangibly breaking bulbous tip (120) away from dilation catheter (100).

FIGS. 4 and 5A show dilation catheter (100) in a mode where dilation catheter (100) is particularly suited for use in procedures to dilate the Eustachian tube (ET). In this mode, bulbous tip (120) is secured to the distal end of shaft (102). When the operator advances dilation catheter (100) into the Eustachian tube (ET) to thereby position balloon (106) into the Eustachian tube (ET), similar to what is shown in FIG. 3B, bulbous body (122) may eventually engage the isthmus (I) thereby arresting further advancement of dilation catheter (100) into the Eustachian tube (ET). This arresting of further advancement may further provide tactile feedback to the operator, indicating that balloon (106) is positioned in the Eustachian tube (ET). The operator may then inflate balloon (106) to thereby dilate the Eustachian tube (ET). During this time, to the extent that guidewire (30) is even positioned within lumen (110) of shaft (102), guidewire (30) may be positioned such that distal end (32) of guidewire (30) is proximal to bulbous tip (120).

After the operator has finished dilating the Eustachian tube (ET), the operator may then wish to dilate a sinus ostium (O) or other passageway associated with drainage of a paranasal sinus. To facilitate such an operation, the operator may remove bulbous tip (120) at mark (140). In some instances, this removal may comprise cutting dilation catheter (100) at mark (140). In some other instances, this removal may comprise breaking dilation catheter (100) at mark (140). In any case, after bulbous tip (120) is removed, dilation catheter (100) may appear as shown in FIG. 5B. At this point, dilation catheter (100) as an open distal end (150) that is proximal to the location where bulbous tip (120) was located. This open distal end (150) provides sufficient clearance for distal end (32) of guidewire (30) to pass freely through open distal end (150) of dilation catheter, as shown in FIG. 5C. With dilation catheter (100) in the mode shown in FIGS. 5B-5C, distal end (150) may also pass through a sinus ostium (O) or other passageway associated with drainage of a paranasal sinus, thereby facilitating use of dilation catheter (100) to perform the procedure shown in FIG. 2A.

IV. EXEMPLARY INSTRUMENT FOR CUTTING DISTAL TIP OFF OF DILATION CATHETER

As noted above, dilation catheter (100) is configured to enable removal of bulbous tip (120) in order to transition dilation catheter (100) from a mode for dilating a Eustachian tube (ET) to a mode for dilating a sinus ostium (O) or other passageway associated with drainage of a paranasal sinus. While it may be possible for an operator to use a conventional knife, scissors, or other cutting instrument to remove bulbous tip (120), or even to break off bulbous tip (120), the relatively small size (e.g., diameter) of distal end (104) may make it somewhat difficult for an operator to successfully sufficiently distal end (104) in order to remove bulbous tip (120). It may therefore be desirable to provide an instrument that is dedicated to cutting bulbous tip (120), with such an instrument providing sufficient stabilization to distal end (104) during the process and providing features that ensure that distal end (104) is cut at the appropriate location to remove bulbous tip (120) without damaging balloon (106) or other features of dilation catheter. FIGS. 6-13E show an example of such an instrument (200).

Instrument (200) of the present example includes a base housing (210), an actuator (250), and a blade (290). Blade (290) is fixedly secured to actuator (250), which is slidably received in base housing (210). Each of these components will be described in greater detail below. As will also be described in greater detail below, distal end (104) of dilation catheter (100) may be inserted into instrument (200), and then blade (290) may be driven by actuator (250) to sever bulbous tip (120) from distal end (104) while base housing (210) supports the rest of distal end (104).

As shown in FIGS. 6-7 and 11-12, base housing (210) includes a support surface (212) defining a support recess (214), with a tip-receiving recess (220) positioned distal to support recess (214). As described in greater detail below, support surface (212) is configured to support distal end (104) of dilation catheter (100) when distal end (104) is inserted into instrument (200). Support recess (214) is configured to align with tip-receiving recess (220) and thereby assist in guiding bulbous tip (120) into tip-receiving recess (220). In the present example, support recess (214) has a generally U-shaped profile. In some other versions, support recess (214) has a radiused or otherwise curved profile.

Base housing (210) further includes a pair of lateral channels (230), with retainer bosses (232) (FIG. 12) being positioned in respective lateral channels (230). Base housing (210) also includes a pair of guide channels (240) positioned distal to support recess (214) and proximal to tip-receiving recess (220). Channels (230, 240) are configured to interact with complementary features of actuator (250) as will be described in greater detail below.

As shown in FIGS. 6-10, actuator (250) of the present example includes an engagement flange (252), a lower recess (260), a pair of downwardly protruding guide prongs (262), and a pair of downwardly protruding latch arms (270). Engagement flange (252) is configured to be engaged by a hand of an operator to facilitate driving of actuator (250) downwardly toward base housing (210) as will be described in greater detail below. Lower recess (260) is configured to complement support recess (214) and thereby provide clearance for a portion of distal end (104) of dilation catheter (100) when actuator (250) is actuated to sever bulbous tip (120) from distal end (104). Guide prongs (262) are configured to slidably fit in guide channels (240) of base housing (210) to thereby maintain alignment between actuator (250) and base housing (210) as actuator (250) transitions between the non-actuated state and the actuated state. Latch arms (270) are configured to slidably fit in lateral channels (230) of base housing (210). The free end of each latch arm (270) includes a latch head (272), which is configured to engage retainer boss (232) in each corresponding lateral channel (230) of base housing (210). Latch heads (272) and retainer bosses (232) cooperate to restrict upward movement of actuator (250) relative to base housing (210).

Figure 9:
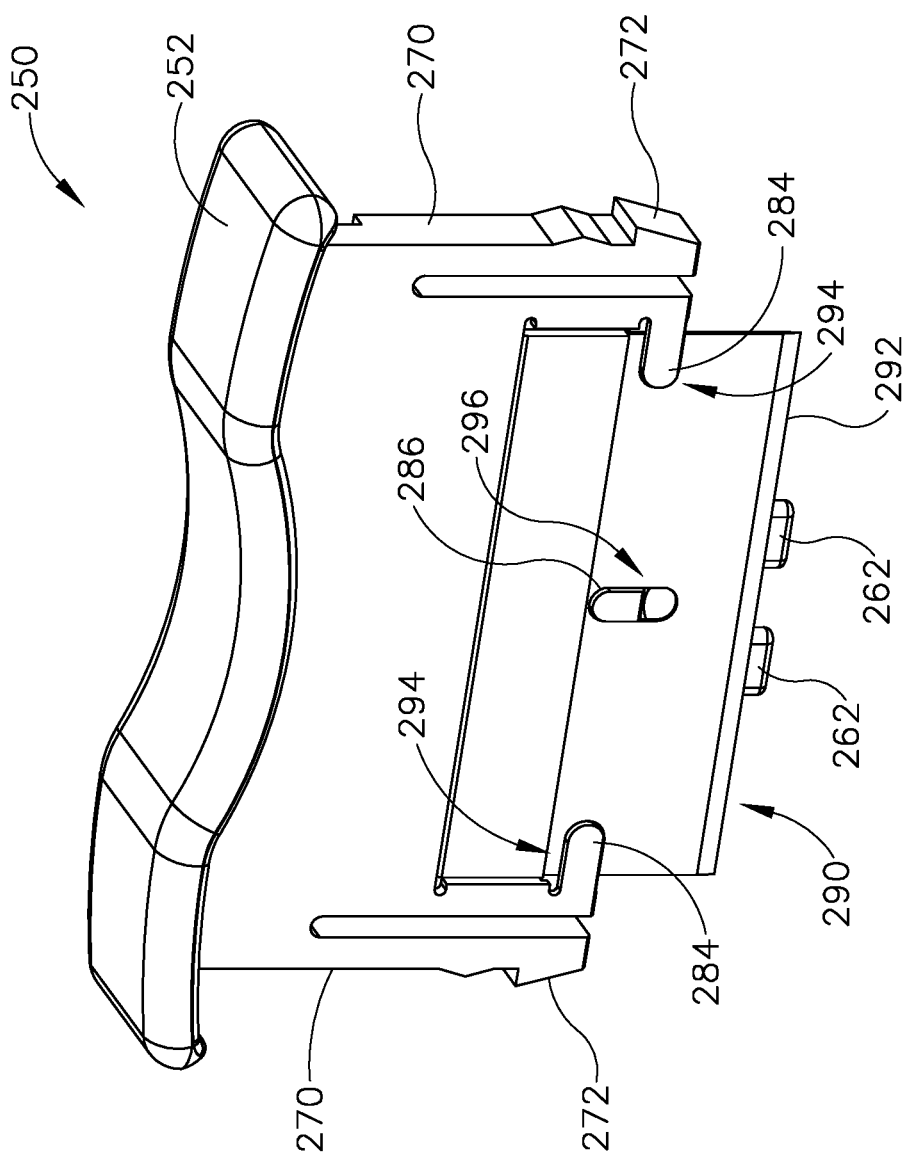
FIG. 9 depicts another perspective view of the actuator and blade assembly of FIG. 8.
Figure 10:
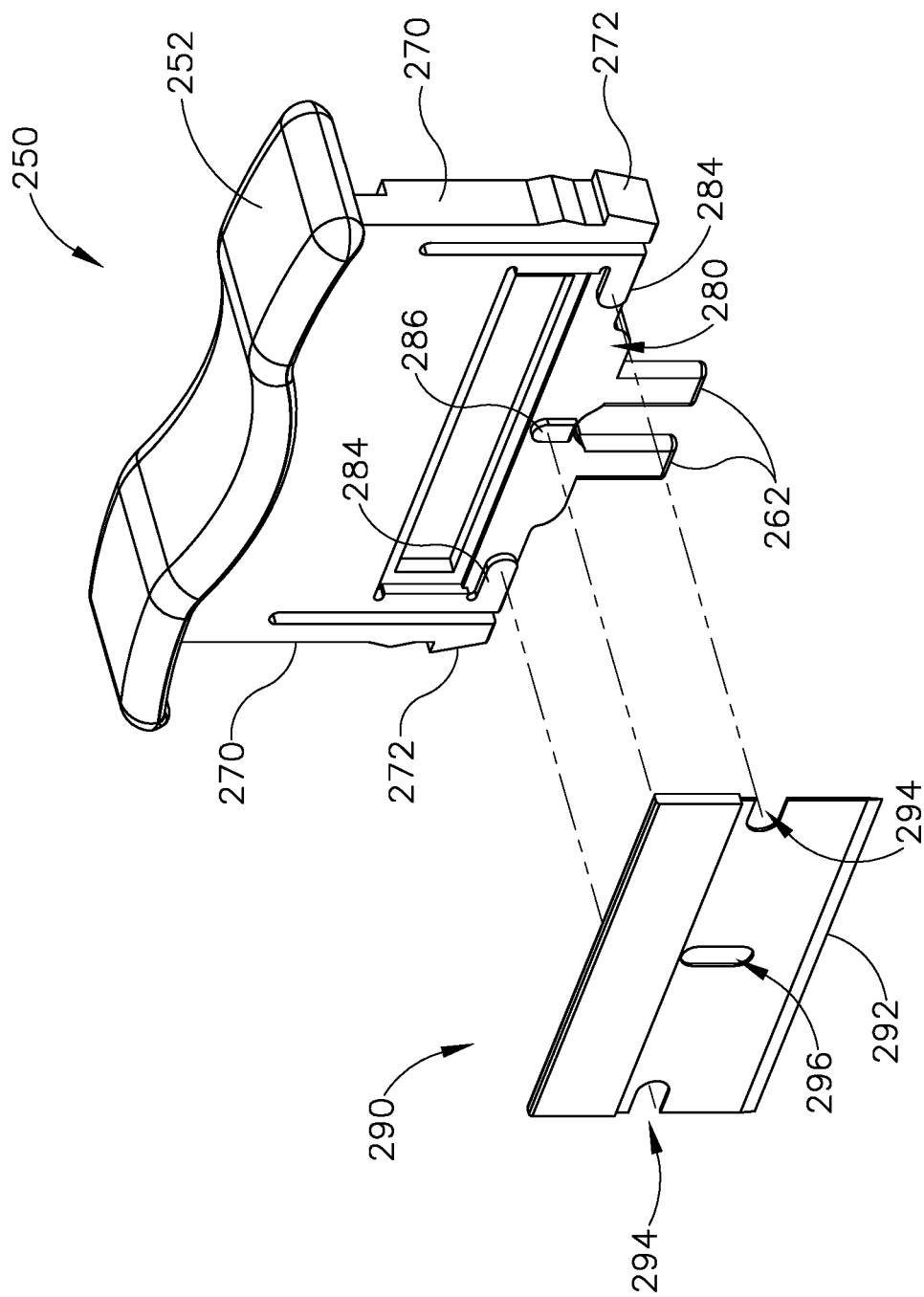
FIG. 10 depicts an exploded perspective view of the actuator and blade assembly of FIG. 8.
Figure 11:
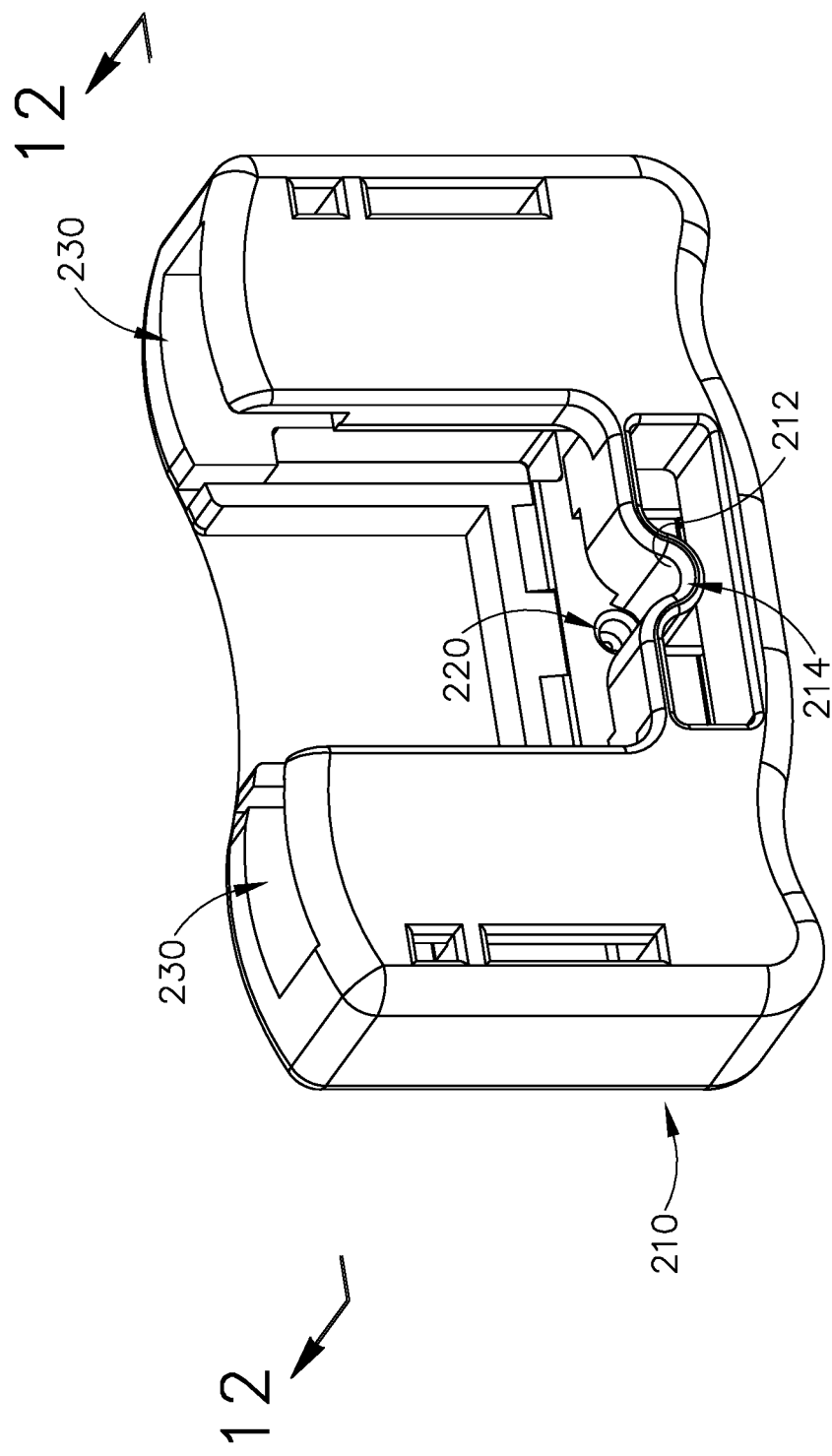
FIG. 11 depicts a perspective view of a base housing of the instrument of FIG. 6.
Figure 12:
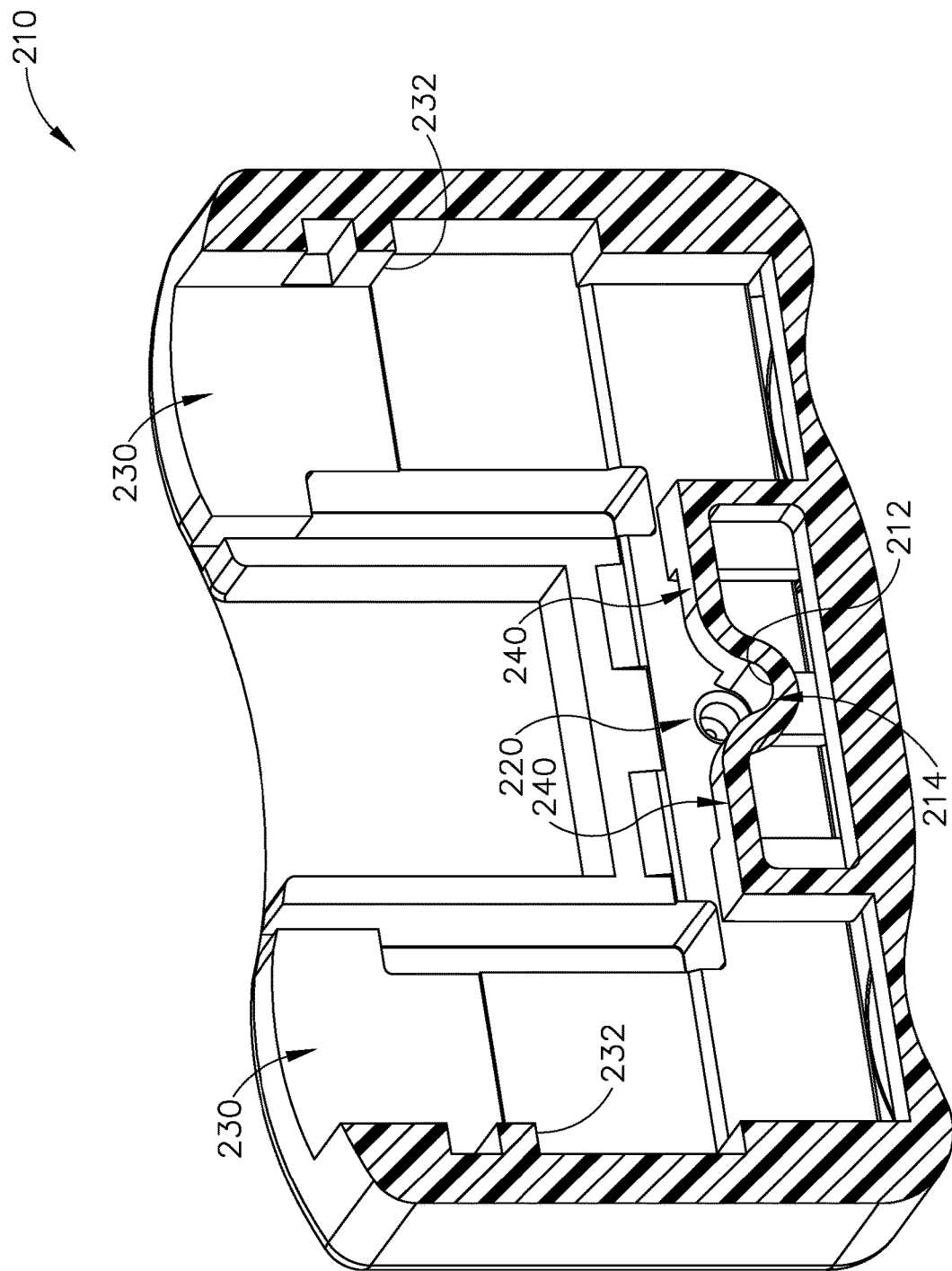
FIG. 12 depicts a cross-sectional view of the base housing of FIG. 11, taken along line 12-12 of FIG. 11.

As shown in FIGS. 7-10, blade (290) of the present example is a conventional single-edge razor blade, including a sharp edge (292), a pair of lateral notches (294), and a central opening (296). As best seen in FIGS. 9-10, blade (290) fits against a distal side of actuator (250). This side of actuator (250) includes a pair of lateral bosses (284) that fit in lateral notches (294) of blade (290); and a central boss (286) that fits in central opening (296). Bosses (284, 286) fit in notches (924) and opening (296) to secure blade (290) to actuator (250) and maintain alignment of blade (290) relative to actuator (250). The fit between blade (290) and actuator (250) provides exposure of sharp edge (292) relative to actuator (250).

Figure 13A:
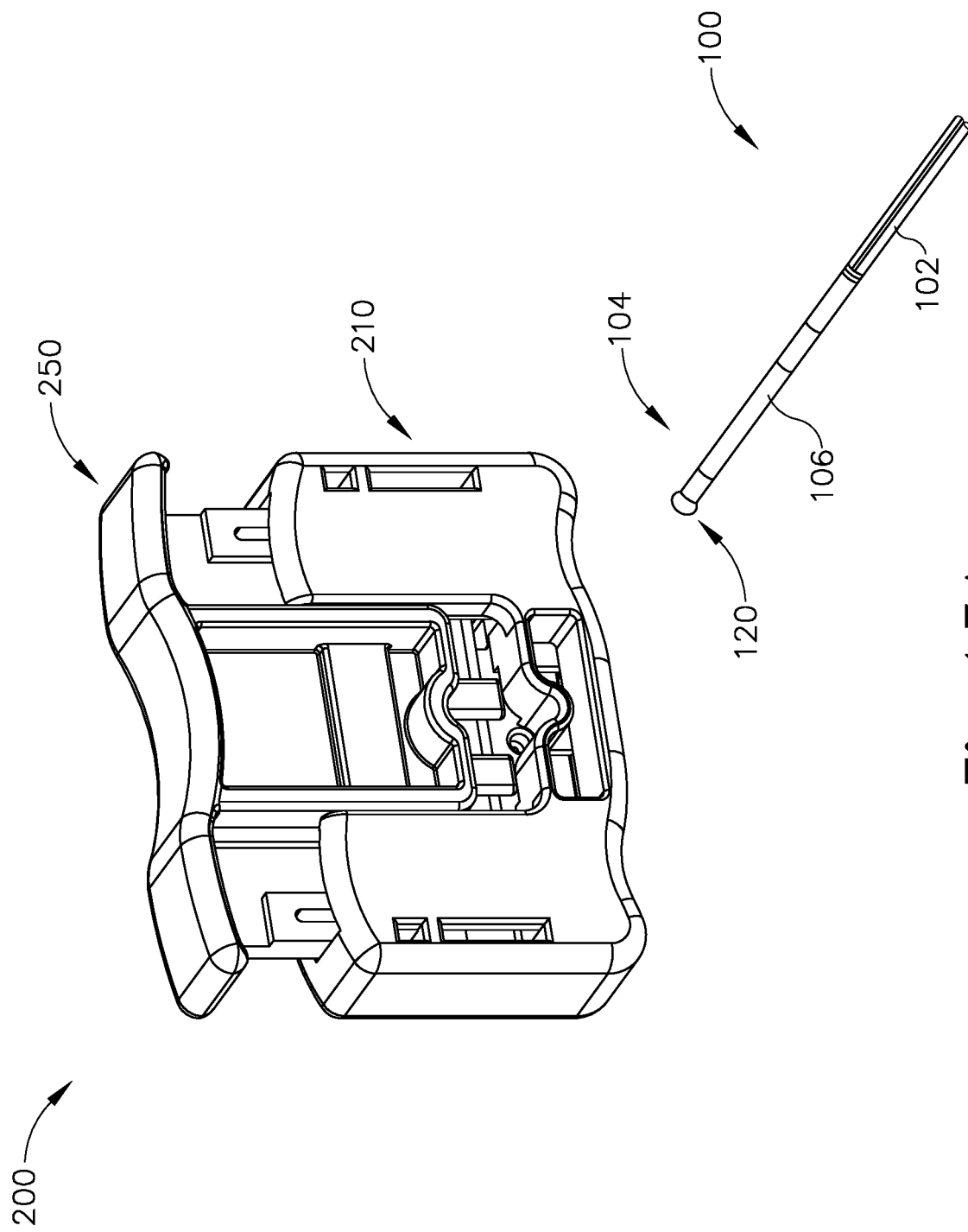
FIG. 13A depicts a perspective view of the dilation catheter of FIG. 4 positioned for insertion in the instrument of FIG. 6, with the actuator and blade assembly in a pre-actuated state.
Figure 13B:
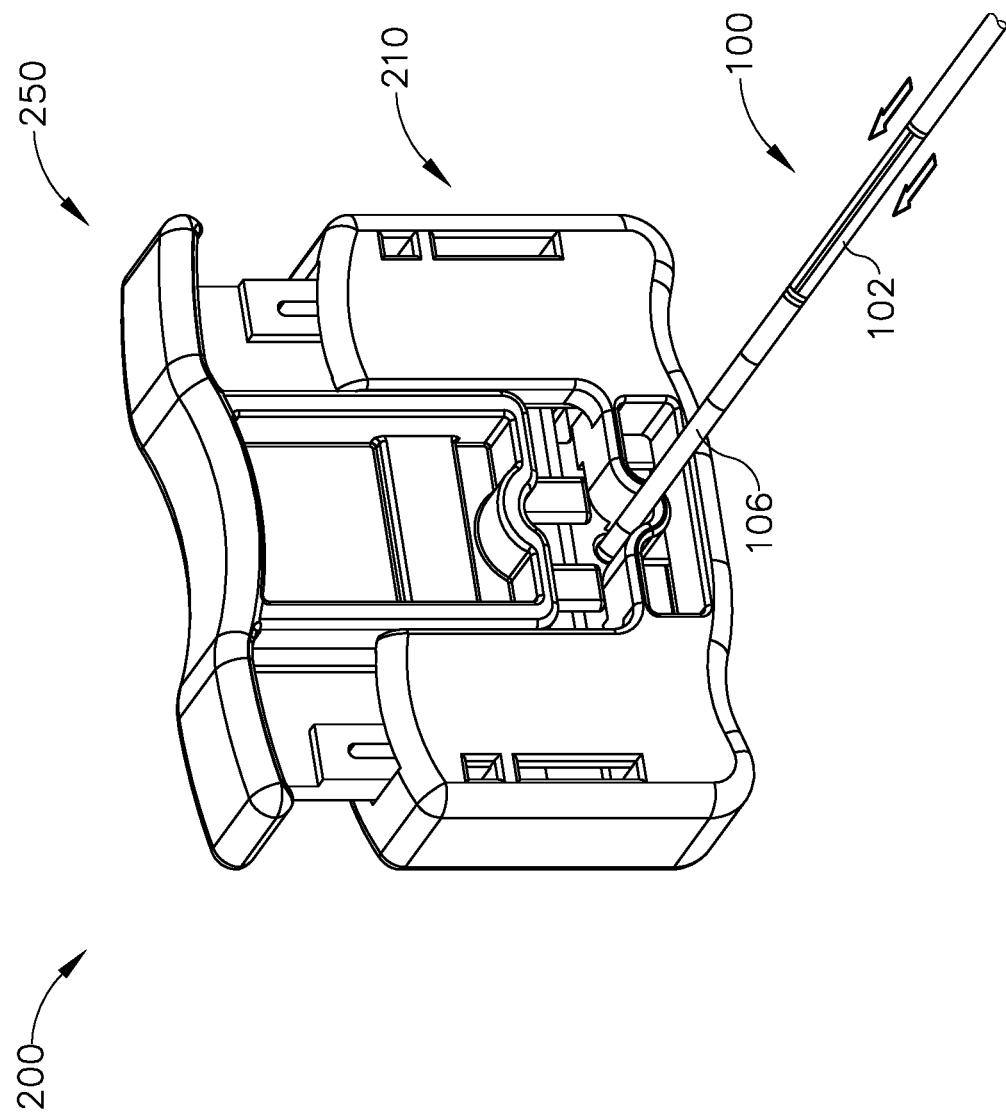
FIG. 13B depicts a perspective view of the dilation catheter of FIG. 4 inserted into the instrument of FIG. 6, with the actuator and blade assembly in the pre-actuated state.
Figure 13C:
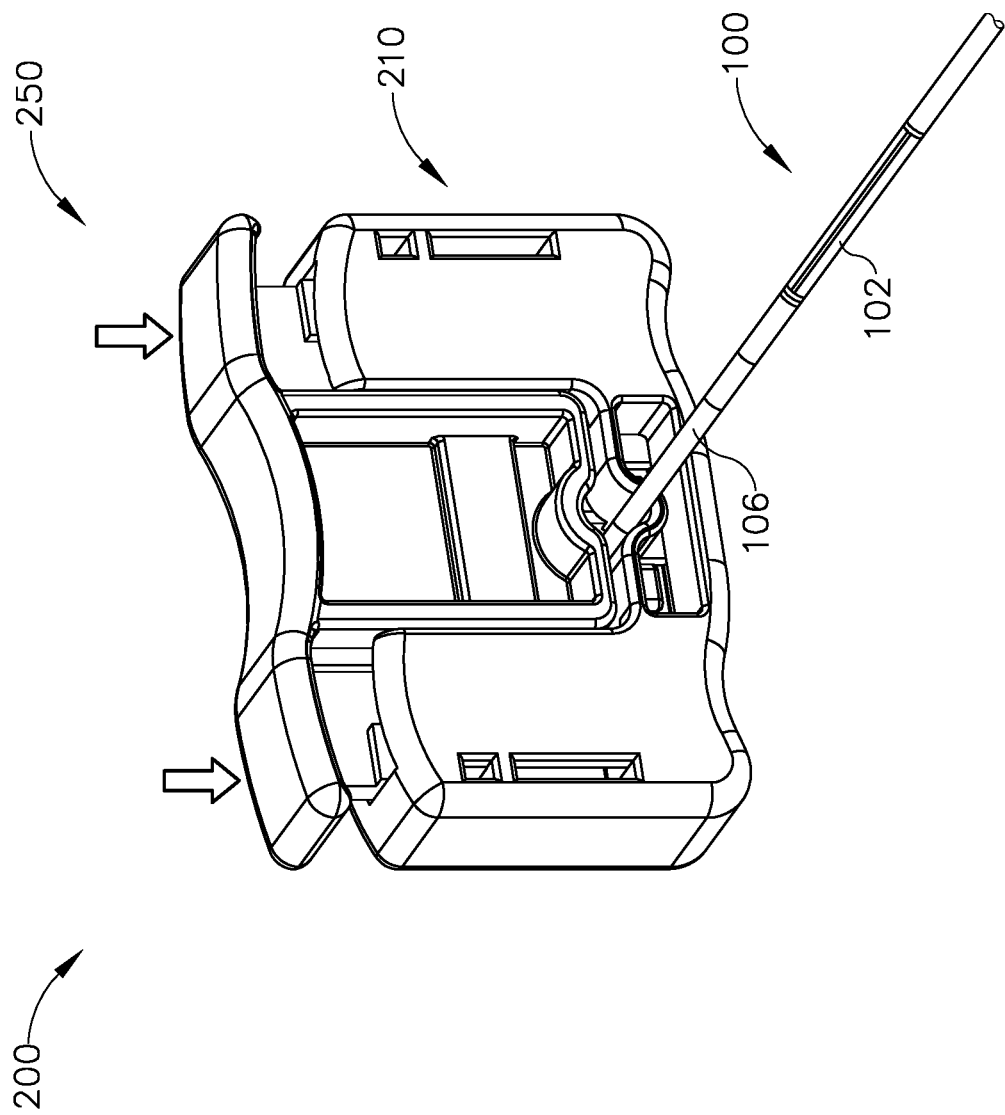
FIG. 13C depicts a perspective view of the dilation catheter of FIG. 4 inserted into the instrument of FIG. 6, with the actuator and blade assembly in an actuated state.

FIGS. 13A-13E show instrument (200) being used to remove bulbous tip (120) from distal end (104) of dilation catheter (100). As shown in FIG. 13A, the operator first aligns dilation catheter (100) such that distal end (104) lies on a common longitudinal axis with tip-receiving recess (220) of base housing (210). The operator then urges dilation catheter (100) distally to position bulbous tip (120) in tip-receiving recess (220), as shown in FIG. 13B. The portion of distal end (104) that is proximal to bulbous tip (120) rests on support surface (212) at support recess (214). The operator then engages engagement flange (252) of actuator (250) and thereby urges actuator (250) downwardly while base housing (210) and dilation catheter (100) remain stationary, as shown in FIG. 13C. As actuator (250) and blade (290) translate downwardly, sharp edge (292) severs distal end (104) to thereby cut off bulbous tip (120). As shown in FIG. 13C, with actuator (250) in the actuated state, lower recess (260) of actuator (250) provides clearance for portion of distal end (104) that is proximal to bulbous tip (120), thereby avoiding the crushing of distal end (104) by actuator (250).

Figure 13D:
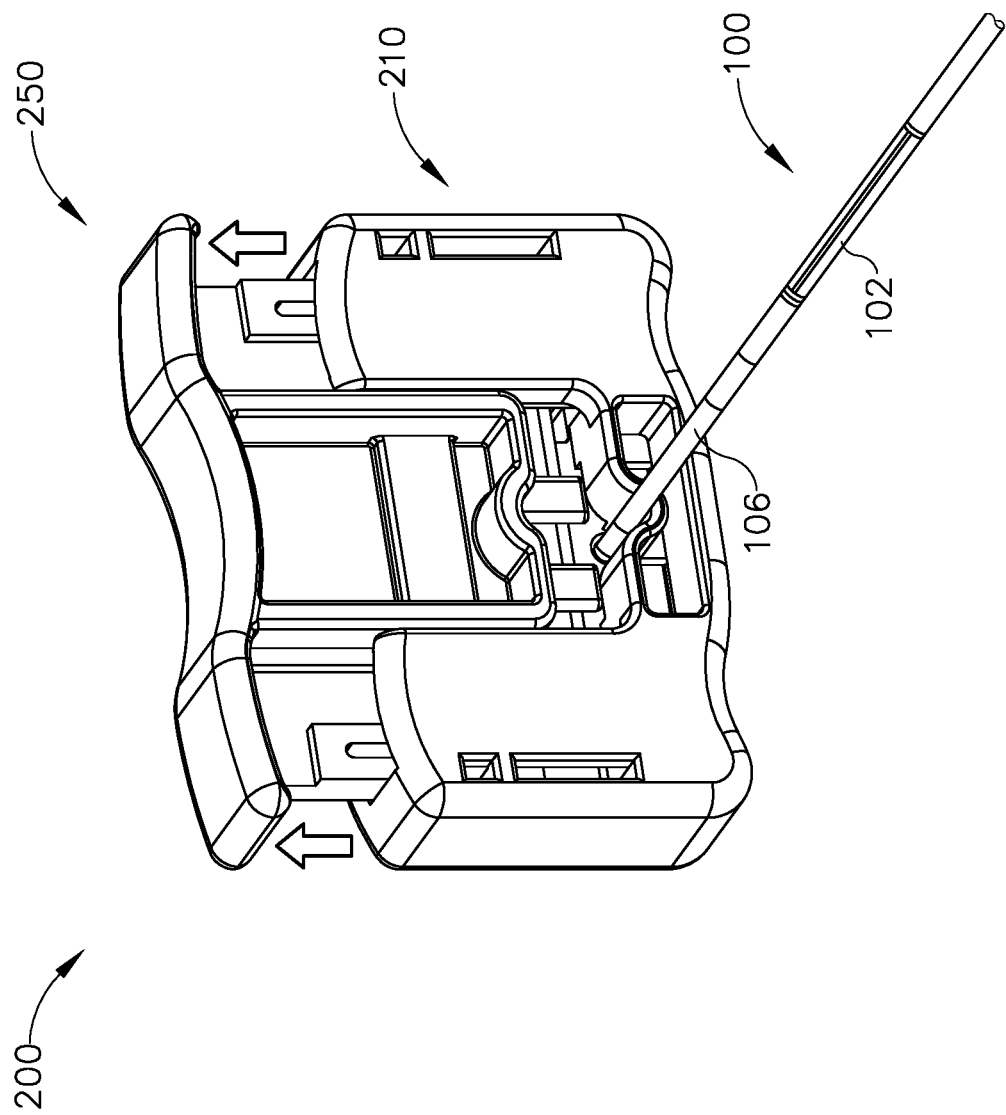
FIG. 13D depicts a perspective view of the dilation catheter of FIG. 4 inserted into the instrument of FIG. 6, with the actuator and blade assembly in a post-actuated state.
Figure 13E:
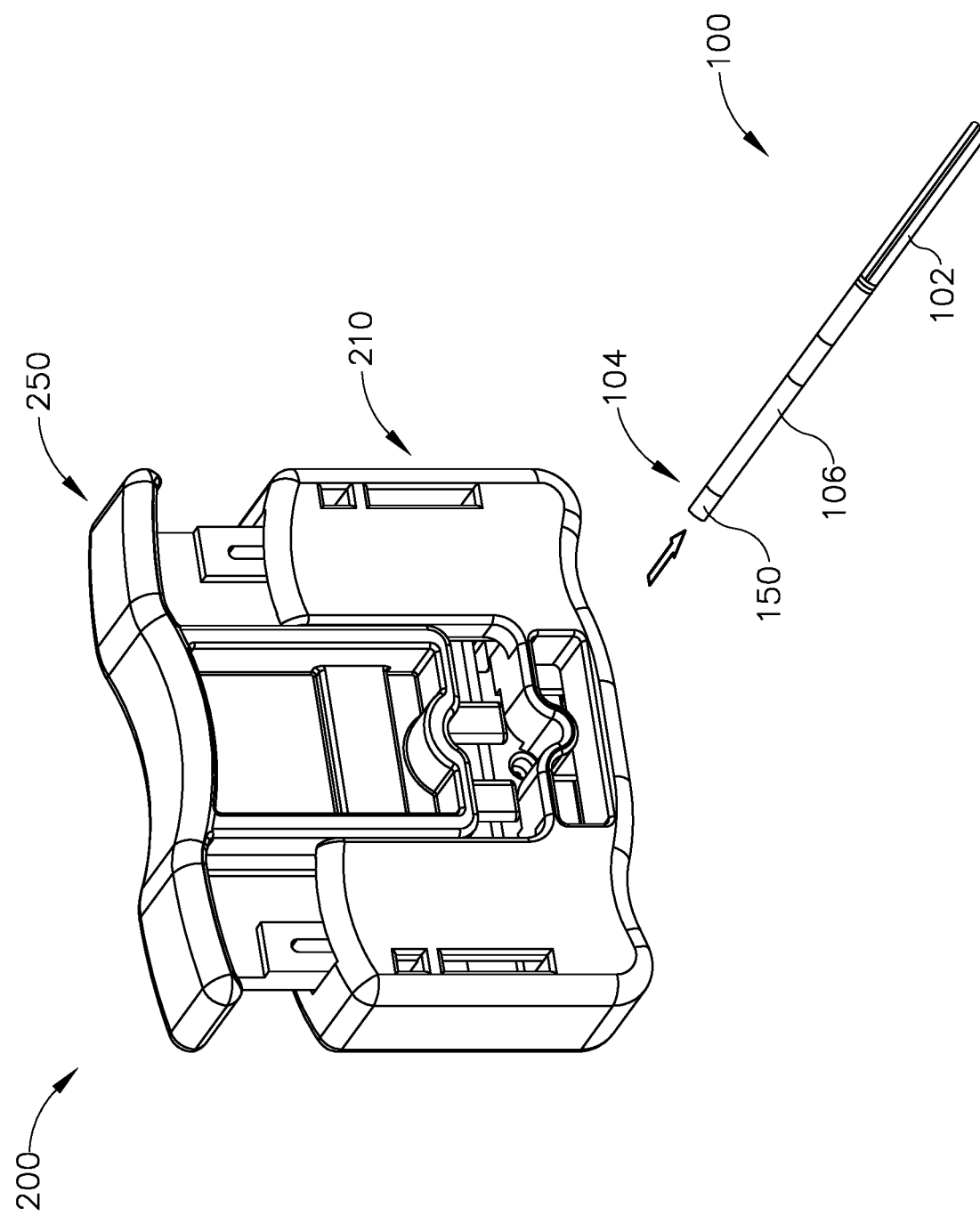
FIG. 13E depicts a perspective view of the dilation catheter of FIG. 4 removed from the instrument of FIG. 6, with the actuator and blade assembly in the post-actuated state.

After achieving the actuated state shown in FIG. 13C, the operator may then release actuator (250) or otherwise urge actuator (250) upwardly to return to the non-actuated position shown in FIG. 13D. In some versions, a spring or other resilient member (not shown) is disposed in base housing (210) to resiliently bias actuator (250) to the non-actuated position. With bulbous tip (120) now severed from distal end (104), the operator may remove dilation catheter (100) from instrument (200) as shown in FIG. 13E and use dilation catheter (100) in a medical procedure.

It should be understood that instrument (200) may be used in the process shown in FIGS. 13A-13E to transition dilation catheter (100) from a mode for dilating a Eustachian tube (ET) to a mode for dilating a sinus ostium (O) or other passageway associated with drainage of a paranasal sinus.

By providing the combination of support surface (212), support recess (214), and integral blade (290), instrument (200) may substantially improve the ease, quality, and consistency of cutting bulbous tip (120) from distal end (104). Moreover, instrument (200) is configured to keep sharp edge (292) effectively covered or shielded, thereby preventing the operator from inadvertently cutting himself or herself with sharp edge (292) during operation of instrument (200).

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) base housing defining: (i) an upwardly presented support surface, and (ii) a distally oriented tip receiving recess, wherein the distally oriented tip receiving recess is sized and configured to receive a bulbous distal tip of a dilation catheter; (b) an actuator movably coupled with the base housing; and (c) a blade secured to the actuator, wherein the actuator is operable to move the blade downwardly relative to the base housing, wherein the blade is configured to sever a portion of a dilation catheter along a plane longitudinally interposed between the support surface and the tip receiving recess to thereby sever the bulbous distal tip of the dilation catheter in response to movement of the actuator relative to the base housing.

Example 2

The apparatus of Example 1, wherein the upwardly presented support surface defines a downwardly extending support recess, wherein the downwardly extending support recess is positioned to correspond with the distally oriented tip receiving recess.

Example 3

The apparatus of Example 2, wherein the downwardly extending support recess has a generally U-shaped profile.

Example 4

The apparatus of any one or more of Examples 2 through 3, wherein the actuator defines an upwardly extending lower recess, wherein the upwardly extending lower recess is positioned to correspond with the downwardly extending support recess.

Example 5

The apparatus of any one or more of Examples 1 through 4, wherein the actuator is operable to translate downwardly relative to the base housing to thereby drive the blade downwardly relative to the base housing.

Example 6

The apparatus of Example 5, wherein the actuator comprises a flange configured for engagement by an operator to drive the actuator downwardly relative to the base housing.

Example 7

The apparatus of any one or more of Examples 1 through 6, wherein the base housing further includes a pair of lateral channels, wherein the lateral channels of the base housing are configured to receive corresponding lateral portions of the actuator.

Example 8

The apparatus of Example 7, wherein the lateral portions of the actuator comprise latch arms configured to fit in the lateral channels of the base housing.

Example 9

The apparatus of Example 8, wherein each latch arm comprises a latch head, wherein each lateral channel comprises a retainer boss, wherein the retainer bosses are configured to cooperate with the latch heads to restrict upward movement of the actuator relative to the base housing.

Example 10

The apparatus of any one or more of Examples 1 through 9, wherein the blade includes a sharp edge, wherein the sharp edge is configured to traverse an axis extending proximally from the distally oriented tip receiving recess.

Example 11

The apparatus of Example 10, wherein the base housing and the actuator are configured to shield the sharp edge of the blade.

Example 12

The apparatus of any one or more of Examples 1 through 11, wherein the blade defines one or both of notches or an opening, wherein the actuator defines at least one boss configured to fit in the one or both of notches or an opening to thereby secure the blade relative to the actuator.

Example 13

The apparatus of any one or more of Examples 1 through 12, further comprising a dilation catheter having a bulbous tip, the bulbous tip being configured to fit in the distally oriented tip receiving recess of the base housing.

Example 14

The apparatus of Example 13, wherein the bulbous tip is configured to fit in a medial region of a Eustachian tube of a human patient, wherein the bulbous tip is configured to not pass through an isthmus of a Eustachian tube of a human patient.

Example 15

The apparatus of any one or more of Examples 13 through 14, wherein a distal portion of the dilation catheter that is proximal to the bulbous distal tip is configured to pass through an ostium of a paranasal sinus of a human patient.

Example 16

An apparatus, comprising: (a) a dilation catheter, the dilation catheter comprising: (i) a shaft, (ii) a dilator at a distal portion of the shaft, and (iii) a bulbous distal tip secured to the shaft at a location distal to the dilator; and (b) a cutting instrument, the cutting instrument comprising: (i) a base housing, the base housing defining: (A) a support surface configured to support the distal portion of the shaft, and (B) a tip receiving recess configured to receive the bulbous tip while the support surface supports the distal portion of the shaft, (ii) an actuator movably coupled with the base housing, and (iii) a blade secured to the actuator, wherein the actuator is operable to drive the blade to sever the bulbous distal tip from the shaft while the support surface supports the distal portion of the shaft and while the bulbous tip is received in the tip receiving recess.

Example 17

The apparatus of Example 16, wherein the support surface is upwardly presented, wherein the actuator is operable to move downwardly relative to the base housing to thereby drive the blade to sever the bulbous distal tip from the shaft.

Example 18

A method, comprising: (a) inserting a distal end of a dilation catheter into a cutting instrument, wherein the cutting instrument includes: (i) a base housing, the base housing defining a distally oriented tip receiving recess, (ii) an actuator movably coupled with the base housing, and (iii) a blade secured to the actuator; (b) actuating the actuator to thereby drive the blade to sever a distal tip from the dilation catheter; and (c) removing the distal end of the dilation catheter from the cutting instrument.

Example 19

The method of Example 18, wherein the distal tip is bulbous, wherein the removed distal end has a smaller outer diameter than the inserted distal end due to the severing of the bulbous distal tip from the dilation catheter.

Example 20

The method of any one or more of Examples 18 through 19, further comprising: (a) using the dilation catheter to dilate a Eustachian tube of a patient before the act of inserting; and (b) using the dilation catheter to dilate a passageway associated with drainage of a paranasal sinus of the patient after the act of removing.

VI. MISCELLANEOUS

It should be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using an apparatus, the apparatus comprising:
   (a) base housing defining:
      (i) an upwardly presented support surface configured to support and contact a distal end of a dilation catheter, the upwardly presented support surface forming a channel such that an upper portion of the distal end of the dilation catheter is unconstrained above the upwardly presented support surface by the base housing, and
      (ii) a distally oriented tip receiving recess tip receiving recess being sized and configured to receive a bulbous distal tip of the dilation catheter, the support surface being aligned with the receiving recess and is thereby positioned and configured to guide the bulbous distal tip of the dilation catheter into the receiving recess;
   (b) an actuator movably coupled with the base housing; and
   (c) a blade secured to the actuator;
the method comprising:
   (a) using the dilation catheter to dilate a Eustachian tube of a patient;
   (b) inserting the bulbous distal tip of the dilation catheter into the distally oriented tip receiving recess of the apparatus;
   (c) actuating the actuator to thereby drive the blade downwardly relative to the base housing to sever the bulbous distal tip from the dilation catheter along a plane longitudinally interposed between the support surface and the tip receiving recess;
   (d) removing the dilation catheter from the apparatus; and
   (e) using the dilation catheter to dilate a passageway associated with drainage of a paranasal sinus of the patient after the act of removing.

2. The method of claim 1, arranging the upwardly presented support surface defining a downwardly extending support recess and the downwardly extending support recess being positioned to correspond with the distally oriented tip receiving recess.

3. The method of claim 2, providing the downwardly extending support recess having a generally U-shaped profile.

4. The method of claim 2, providing the actuator with an upwardly extending lower recess being positioned to correspond with the downwardly extending support recess.

5. The method of claim 1, operating the actuator to translate downwardly relative to the base housing to thereby drive the blade downwardly relative to the base housing.

6. The method of claim 5, providing the actuator with a flange configured for engagement by an operator to drive the actuator downwardly relative to the base housing.

7. The method of claim 1, providing the base housing with a pair of lateral channels receiving corresponding lateral portions of the actuator.

8. The method of claim 7, providing lateral portions of the actuator with latch arms fitting in the lateral channels of the base housing.

9. The method of claim 8, providing each latch arm with a latch head and each lateral channel comprising a retainer boss cooperating with the latch heads to restrict upward movement of the actuator relative to the base housing.

10. The method of claim 1, providing the blade with a sharp edge configured to traverse an axis extending proximally from the distally oriented tip receiving recess.

11. The method of claim 10, shielding the sharp edge of the blade by the base housing and the actuator.

12. The method of claim 1, providing the blade with one or both of notches or an opening and the actuator including at least one boss fitting in the one or both of notches or an opening to thereby secure the blade relative to the actuator.

13. The method of claim 1, fitting the bulbous distal tip in a medial region of a Eustachian tube of a human patient, the bulbous distal tip being configured to not pass through an isthmus of a Eustachian tube of a human patient.

14. The method of claim 1, positioning a distal portion of the dilation catheter that is proximal to the bulbous distal tip to pass through an ostium of a paranasal sinus of a human patient.

15. A method of using an apparatus, the apparatus, comprising:
  (a) a dilation catheter, the dilation catheter comprising:
    (i) a shaft,
    (ii) a dilator at a distal portion of the shaft, and
    (iii) a bulbous distal tip secured to the shaft at a location distal to the dilator, the bulbous distal tip being configured to prevent the distal portion of the shaft from otherwise traversing a sinus ostium or an isthmus between a Eustachian tube and a middle ear, the distal portion of the shaft being configured to traverse the sinus ostium in the absence of the bulbous distal tip; and
  (b) a cutting instrument, the cutting instrument comprising:
    (i) a base housing, the base housing defining:
      (A) a support surface configured to support the distal portion of the shaft,
      (B) a tip receiving recess configured to receive the bulbous tip while the support surface supports the distal portion of the shaft,
      (C) a first guide channel positioned adjacent to a first side of the support surface, and
      (D) a second guide channel positioned adjacent to a second side of the support surface,
    (ii) an actuator movably coupled with the base housing, the actuator including:
      (A) a first guide prong, the first guide channel being configured to slidably receive the first guide prong, and
      (B) a second guide prong, the second guide channel being configured to slidably receive the second guide prong,
      the first guide channel, the first guide prong, the second guide channel, and the second guide prong being configured to cooperate to maintain alignment between the base housing and the actuator, and
    (iii) a blade including an opening, the actuator being secured to the blade at the opening, the actuator being operable to drive the blade to sever the bulbous distal tip from the shaft while the support surface supports the distal portion of the shaft and while the bulbous tip is received in the tip receiving recess,
    the distal portion of the shaft being configured to traverse the sinus ostium after the bulbous distal tip is severed from the shaft by the cutting instrument;
  the method comprising:
    (a) using the dilation catheter to dilate a Eustachian tube of a patient;
    (b) inserting the bulbous distal tip of the dilation catheter into the tip receiving recess of the cutting instrument;
    (c) actuating the actuator to thereby drive the blade to sever the bulbous distal tip from the dilation catheter;
    (d) removing the dilation catheter from the cutting instrument; and
    (e) using the dilation catheter to dilate a passageway associated with drainage of a paranasal sinus of the patient after the act of removing.

16. The method of claim 15, moving the actuator downwardly relative to the base housing to thereby drive the blade to sever the bulbous distal tip from the shaft.

17. A method, comprising:
  (a) using a dilation catheter to dilate a Eustachian tube of a patient;
  (b) inserting a distal end of the dilation catheter into a cutting instrument after using the dilation catheter to dilate the Eustachian tube of the patient, the cutting instrument including:
    (i) a base housing, the base housing defining a distally oriented tip receiving recess,
    (ii) an actuator movably coupled with the base housing, and
    (iii) a blade secured to the actuator;
  (c) actuating the actuator to thereby drive the blade to sever a distal tip from the dilation catheter;
  (d) removing the distal end of the dilation catheter from the cutting instrument; and
  (e) using the dilation catheter to dilate a passageway associated with drainage of a paranasal sinus of the patient after the act of removing.

18. The method of claim 17, providing the distal tip being bulbous, the removed distal end having a smaller outer diameter than the inserted distal end due to the severing of the bulbous distal tip from the dilation catheter.

19. The method of claim 17, including a mark on the dilation catheter for indicating where to sever the distal tip form the dilation catheter.

* * * * *